United States Patent
Kita et al.

(10) Patent No.: US 7,454,952 B2
(45) Date of Patent: Nov. 25, 2008

(54) METHOD AND APPARATUS FOR MONITORING MERCURY IN A GAS SAMPLE

(75) Inventors: Dieter Kita, Blackstone, MA (US); James H. Grassi, Westwood, MA (US); Jeffrey Socha, Berlin, MA (US); Dirk Appel, Salem, MA (US)

(73) Assignee: Thermo Fisher Scientific Inc., Waltham, MA (US)

( * ) Notice: Subject to any disclaimer, the term of this patent is extended or adjusted under 35 U.S.C. 154(b) by 751 days.

(21) Appl. No.: 11/120,182

(22) Filed: May 2, 2005

(65) Prior Publication Data

US 2006/0245973 A1     Nov. 2, 2006

(51) Int. Cl.
*G01N 7/00* (2006.01)
(52) U.S. Cl. .................................. 73/31.03
(58) Field of Classification Search ............. 73/31.03
See application file for complete search history.

(56) References Cited

U.S. PATENT DOCUMENTS

| | | | |
|---|---|---|---|
| 5,597,535 A | 1/1997 | Schaedlich et al. | |
| 5,900,042 A | 5/1999 | Mendelsohn et al. | 75/742 |
| 6,475,802 B2 | 11/2002 | Schaedlich et al. | |
| 6,852,542 B2 | 2/2005 | Mandel et al. | 436/81 |
| 7,037,725 B2 | 5/2006 | Mandel et al. | 436/81 |
| 2002/0068030 A1 | 6/2002 | Nolan et al. | 423/210 |
| 2006/0243096 A1* | 11/2006 | Kita et al. | 75/670 |
| 2006/0245974 A1* | 11/2006 | Kita et al. | 422/68.1 |

OTHER PUBLICATIONS

Carter, Christopher C. Ph.D., "A Cavity Ring-Down Spectroscopy Mercury Continuous Emission Monitor", Quarterly Technical Progress Report, for the period Jan. 1, 2003, ending Mar. 31, 2003; pp. 1-23.
International Search Report, Aug. 7, 2007, p. 1.

* cited by examiner

*Primary Examiner*—Hezron E. Williams
*Assistant Examiner*—Rodney T Frank
(74) *Attorney, Agent, or Firm*—Chapin IP Law, LLC; Barry W. Chapin, Esq.

(57) ABSTRACT

Disclosed are a system and method for monitoring total mercury within a gas sample in a substantially continuous manner and for calibrating for both elemental and oxidized mercury. A converter of the Continuous Emission Monitoring System (CEMS) receives a gas sample containing vaporized mercury from a probe. The converter converts oxidized mercury present within the gas sample into an elemental mercury component and an oxidizing component using thermal cracking. The converter also reduces the pressure of the gas sample to minimize recombination of the elemental mercury component with the oxidizing components. A mercury analyzer of the system receives the reduced pressure gas sample from the converter and detects the fluorescence of the elemental mercury within the sample. The mercury analyzer holds the gas sample at the reduced pressure to reduce an effect of fluorescence quenching on the fluorescence of the elemental mercury within the sample and provides substantially accurate measurement of the concentration of the elemental mercury in the gas sample.

28 Claims, 14 Drawing Sheets

METHOD AND APPARATUS FOR MONITORING MERCURY IN A GAS SAMPLE

RELATED APPLICATIONS

This application relates to U.S. patent application Ser. No. 11/120,315, entitled "METHOD AND APPARATUS FOR CONVERTING OXIDIZED MERCURY INTO ELEMENTAL MERCURY", U.S. patent application Ser. No. 11/120,317, entitled "METHOD AND APPARATUS FOR DETECTING THE PRESENCE OF ELEMENTAL MERCURY IN A GAS SAMPLE", and U.S. patent application Ser. No. 11/120,316, entitled "METHOD AND APPARATUS FOR GENERATING OXIDIZED MERCURY HAVING A MEASURABLE CONCENTRATION", all filed on even date herewith, the entire teachings of which are incorporated herein by reference.

FIELD OF THE INVENTION

Embodiments of the invention relate to monitoring of mercury-containing compounds, and more particularly to mercury monitoring by converting mercury in such compounds to elemental mercury and by using fluorescence detection in combination with a mechanism to reduce fluorescence quenching in such compounds to monitor the presence of mercury in gaseous emissions.

BACKGROUND

Emissions from fossil fuel combustion facilities, such as flue gases of coal-fired utilities and municipal solid waste incinerators, include mercury. The emissions include vaporized mercury as elemental mercury, $Hg^0$, or as part of a mercury-containing compound (e.g., oxidized mercury). The oxidized mercury typically occurs as a form of mercury ($Hg^{+2}$), such as mercuric chloride or mercuric nitrate.

Many countries either regulate or are contemplating regulations of emissions of mercury within waste gases because of potential environmental hazards posed by the mercury emissions. Hence facilities that generate gas emissions, which may contain mercury, typically would monitor total mercury concentration in the emissions to comply with the regulations. To detect the total amount of mercury present within emissions generated by a facility, mercury monitoring systems can convert oxidized mercury in a gas sample into elemental mercury and measure the total amount of elemental mercury within the gas sample.

One technique for performing the conversion involves the use of a wet chemical solution containing $SnCl_2$ (i.e., a wet chemistry method) to convert the oxidized mercury of a gas sample into elemental mercury. The technique bubbles a gas emission sample through a through the wet chemical solution to convert $Hg^{+2}$ to $Hg^0$. The resulting elemental concentration is the sum of both the oxidized and elemental forms of mercury.

Another conversion technique involves heating an emission sample, as to temperatures of about 750° C. Heating of the $Hg^{+2}$ within the sample separates or "cracks" the oxidized mercury into an elemental component, $Hg^0$, and an oxidizing component. In certain situations, after the $Hg^{+2}$ within an emission sample is converted into $Hg^0$ using the relatively high temperature, $H_2$ is introduced to react with $O_2$ present within the emission sample. The combination of the $H_2$ with the $O_2$ forms water vapor that, upon immediate collection via a condensing unit, removes the separated oxidizing components or compounds such as HCl and reaction byproducts before they have the opportunity to reoxidize the elemental Hg.

Once the conventional systems convert the oxidized mercury within the emission sample into elemental mercury, the systems can use an analytical technique such as atomic fluorescence spectroscopy to detect the elemental mercury. In atomic fluorescence spectroscopy, a spectrometer detects a concentration of a particular chemical species (e.g., a chemical element or molecule) in a sample by measuring the degree to which atoms of the particular species absorb light of a wavelength, which characterizes the species.

For example, to detect mercury within a gas emission sample, a light source emitting light at 253.7 nm is used to excite mercury atoms within a sample. As the elemental mercury within the gas sample absorbs the light from the light source, the elemental mercury enters an excited state. As the excited elemental mercury decays from the excited state back to a non-excited state, the elemental mercury releases energy by fluorescing light. A detector measures the light fluorescence produced by the sample. The fluorescence represents a measure of the concentration of the elemental mercury in the gas sample.

Certain conventional elemental mercury detectors utilize cold-vapor atomic absorption spectrometry (CVAAS) or cold-vapor atomic fluorescence spectrometry (CVAFS) as detection techniques. The CVAAS and CVAFS detection techniques, however, are susceptible to measurement interferences such as caused by interference gases (e.g., NOx, $SO_2$, HCl, and $Cl_2$) or quenching gases e.g., $N_2$, $O_2$, present within a sample. Elemental mercury detectors utilizing CVAAS or CVAFS detection techniques benefit from the removal of these interference gasses.

In the CVAAS technique, gases (e.g., NOx, $SO_2$, HCl, and $Cl_2$) may cause interference with the measurements made by associated elemental mercury detectors. The gasses absorb light during use of the CVAAS measurement technique. Thus, conventional elemental mercury detectors using the CVAAS measurement technique can provide a false reading. To minimize or remove interference gasses for detectors using the CVAAS technique, for example, elemental mercury detectors utilize a gold trap to minimize or remove the effects of $SO_2$ within a gas sample. The gas sample flows, over time, through the gold trap, the gold material traps elemental mercury present within the gas sample. After the gold trap collects elemental mercury over time, the gold trap is heated and a $SO_2$-free carrier gas is passed over the gold trap to deliver the elemental mercury collected on the gold trap to the detector. The gold trap, therefore, limits the effect of $SO_2$ on the absorption of the elemental mercury and improves measurement sensitivity of the CVAAS detector.

For elemental mercury detectors using the CVAFS technique, fluorescence quenching by gases (e.g., $N_2$, $O_2$) can affect the performance of the detectors. In the CVAFS technique, concentrating devices, such as gold traps, are used to minimize or remove the effect of fluorescence quenching on the measurements made by the detectors. The trap collects elemental mercury over time and maximizes the detection sensitivity of the associated detector. The trapped mercury is then thermally desorbed into a gas stream of Argon, which is a much less efficient quencher than either nitrogen or oxygen. Thus the gas sample can be conditioned to minimize the presence ands effect of fluorescence quenching gases (e.g., $N_2$, $O_2$) on the measurements made by the detector using the CVAFS technique.

SUMMARY

Conventional systems for detecting the total amount of mercury present within emissions have various deficiencies.

As indicated above, the use of a wet chemical solution provides for conversion of oxidized mercury into elemental mercury. However, the wet chemistry method requires continuous expert operator attention, is relatively labor intensive, and may result in a composition having constituents that could interfere with accurate detection of the elemental mercury. Additionally, the wet chemical solution or reagent used in the wet chemistry method typically includes corrosive properties, becomes depleted over time, and requires user monitoring and replenishment.

Also as indicated above, thermal cracking at temperatures at or greater than about 750° C. can be used to convert $Hg^{+2}$ to $Hg_0$. However, if the gas sample then cools, the $Hg^0$ may recombine either with other oxidizing compounds present in the gas sample or with the byproducts of the thermal cracking reaction (e.g., the oxidizing component). Thus a fraction of the $Hg^0$ may convert back to $Hg^{+2}$ before analysis, resulting in an underestimation of the concentration of the mercury within the gas sample.

Addition of $H_2$ gas may prevent such recombination, but its use in a high temperature zone, together with the need to replenish or replace the $H_2$ source, makes this conversion approach not practical for all Hg monitoring applications.

As indicated above, in atomic fluorescence spectroscopy, as elemental mercury within a gas sample absorbs light from a light source (e.g., where the light source of the spectrometer emits light of a relatively narrow wavelength corresponding to the atomic absorption of the elemental mercury), the elemental mercury enters an excited state. As the excited elemental mercury moves from the excited state back to a non-excited state, the elemental mercury releases energy in the form of fluoresced light. However, a process known as "fluorescence quenching" reduces the detectable fluorescence of the elemental mercury.

The mechanism that causes fluorescence quenching is collisional deactivation. In collisional deactivation, an excited mercury atom collides with another atom/molecule within the gas emission sample or with a wall of the spectrometer, and transfers energy with the object of the collision. In so doing, the excited elemental mercury atom surrenders its energy through a non-fluorescent mechanism (i.e., without emitting light). Collisional deactivation reduces the overall fluorescence intensity of the elemental mercury present within the gas sample. Thus, fluorescence quenching can reduce the ability of an atomic fluorescence spectrometer to accurately measure the concentration of elemental mercury in the gas sample.

While collisional deactivation of electronically excited mercury is a general phenomenon, particular molecules are more efficient than others in bringing about non-fluorescence deactivation. Oxygen is a particularly efficient quenching agent. By diluting the sample stream with an oxygen-depleted carrier gas or removing the oxygen through combustion or some other means, the effects of oxygen quenching are minimized and the signal enhanced relative to what would be observed should oxygen be present in the same volume of carrier gas.

Additionally, as described above, certain elemental mercury detection systems, such as those utilizing cold-vapor atomic absorption spectrometry (CVAAS) or cold-vapor atomic fluorescence spectrometry (CVAFS) as detection techniques, collect elemental mercury within a gas emission sample by trapping the elemental mercury on gold material, over a particular time period. At the conclusion of the time period, the elemental mercury detector desorbs the collected, concentrated mercury from the trap and the concentration of mercury within the gas emission sample is detected using a spectrometer. While such a system allows detection of the concentration of mercury within the gas sample, the detection is part of a "batch process" and is not continuous. Thus the described elemental mercury detection system is less likely, depending upon the timing of the batch process, to detect irregularities or changes in the mercury concentration within the gas sample at a particular instant (e.g., "spikes" in the mercury concentration at a particular time or for a particular duration). The described elemental mercury detector instead detects the time averaged mercury concentration for the gas sample.

The present mercury monitoring system is a Continuous Emission Monitoring System (CEMS) that monitors total mercury within a gas sample in a substantially continuous manner. A converter, as used within the system, is configured to receive a gas sample containing vaporized mercury from a probe. The converter decomposes oxidized mercury present within the gas sample into an elemental mercury component and an oxidizing component using thermal cracking. The converter also operates to reduce the pressure of the gas sample to minimize recombination of the elemental mercury component with the oxidizing components. An elemental mercury analyzer of the system receives the gas sample from the converter and detects the elemental mercury, as by measuring the fluorescence of the elemental mercury within the sample. The elemental mercury analyzer contains the gas sample at the reduced pressure to reduce the effect of fluorescence quenching on the fluorescence of the elemental mercury within the sample relative to atmospheric pressure. By reducing the effect of fluorescence quenching, the analyzer provides substantially accurate measurement of the concentration of the elemental mercury in the gas sample.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

The system monitors total mercury within a gas sample in a substantially continuous manner. A converter, as used within the system, is configured to receive a gas sample containing vaporized mercury from a probe. The converter converts oxidized mercury present within the gas sample into an elemental mercury component and an oxidizing component using thermal cracking. The converter also operates to reduce the pressure of the gas sample to minimize recombination of the elemental mercury component with the oxidizing components. An elemental mercury analyzer of the system receives the gas sample from the converter and detects the fluorescence of the elemental mercury within the sample. The elemental mercury analyzer contains the gas sample at the reduced pressure to reduce the effect of fluorescence quenching on the fluorescence of the elemental mercury within the sample. By reducing the effect of fluorescence quenching, the analyzer provides substantially accurate measurement of the concentration of the elemental mercury in the gas sample.

Figure 1:
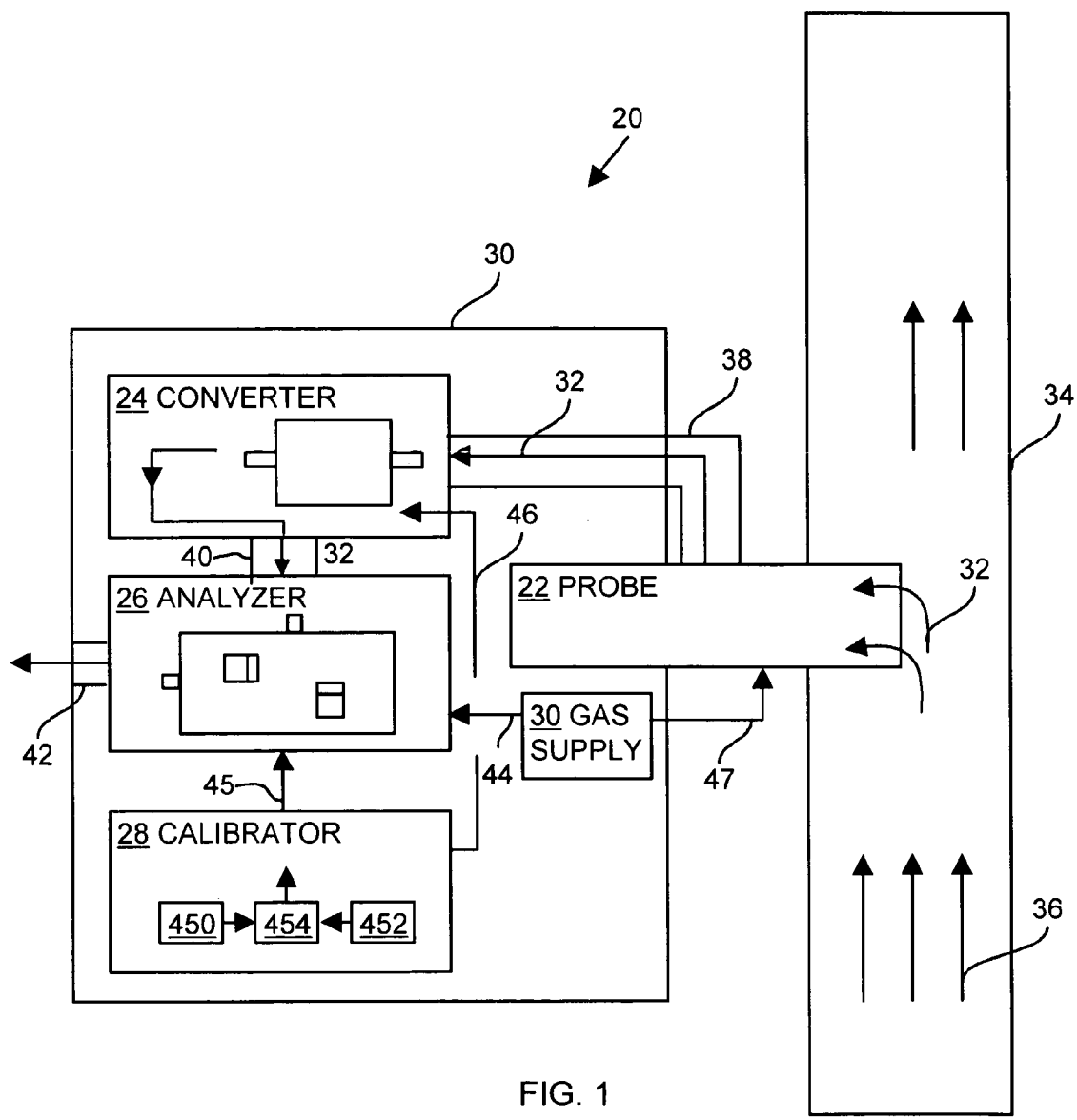
FIG. 1 is a simplified schematic of a mercury monitoring system.

FIG. 1 illustrates a mercury monitoring system 20 for monitoring total mercury within a fluid sample, such as in an effluent gas from a coal-fired power plant, in a substantially continuous manner. The mercury monitoring system 20 defines a Continuous Emission Monitoring System (CEMS). The mercury detection system 20 includes a probe 22, a converter 24, an analyzer 26, and preferably also a calibrator 28 and a gas supply 30.

The probe (e.g., extraction probe) 22 is configured to receive a gas sample 32 from a sample source and deliver the gas sample 32 to the converter 24. For example, the probe 22 extends into or is mounted proximate to a stack or flue 34 of a coal combustion facility and collects, as the gas sample 32, a portion of the fluid or gas (e.g., effluent) 36 flowing through the stack 34. The probe 22 can include an inertial filter that separates particulate matter (e.g., flue ash) from the gas sample 32. Surfaces of the probe 22 that contact the gas sample 32 typically have a coating (e.g., glass) that minimizes or prevents chemical reactions between the probe and mercury present within the gas sample 32. In one arrangement, the inertial filter of the probe 22 includes a heater element (not shown). The heater element can heat the gas sample 32 within the inertial filter.

The probe 22 is connected to the converter 24 by way of a heated conduit 38 maintained at a temperature of, for example, 150° C. The heated conduit 38 limits condensation of the gas sample 32 and "sticking" of vaporized mercury to the conduit 38 and provides efficient transport of the gas sample 32 to the converter. The probe 22 couples to the gas supply 30 via a conduit 47. In one arrangement, the gas supply 30 provides dilution gas, such as air, to the probe 22 to dilute the concentration of mercury within the gas sample 32 prior to delivery of the gas sample 32 to the converter 24. The heated conduit 38 receives heat from a heat source, such as an electrical resistance heater.

The converter 24 receives the gas sample 32 from the probe 22 and is operable to convert the vapor-phase species of mercury (e.g., oxidized mercury) present within the gas sample 32 into elemental mercury and to maintain the mercury in the elemental form so as to allow the analyzer 26 to detect the total mount of mercury present within a gas sample. The converter 24 converts oxidized forms of mercury, $Hg^{+2}$ (e.g., $HgCl_2$, $Hg(NO_3)_2$) into elemental mercury, $Hg^0$, by applying a relatively high temperature to the gas sample 32 and then utilizes a reduced pressure to minimize the converted elemental mercury in the sample from combining with oxidizing compounds or components present within the gas sample 32. A more detailed description of the converter 24 is provided below.

The analyzer 26 is connected to the converter 24 by way of a heated conduit 40 (e.g., to a temperature between approximately 100° C. and 200° C.) and is coupled to a pump or eductor (not shown) to draw the heated and reduced pressure gas sample 32 into and through the converter 24. In one arrangement, the analyzer 26 is an atomic fluorescence analyzer that measures or detects an amount or a concentration of elemental mercury present within the gas sample 32. Upon completion of the detection process, the analyzer 26 exhausts the fluid or gas sample 32 to the atmosphere via an exhaust port 42. A more detailed description of the analyzer 26 is provided below.

Calibration is provided by the calibrator 28 which, in one arrangement is in fluid communication with the analyzer 26 through a line or conduit 45 and provides vaporized elemental mercury to the analyzer 26 at a particular concentration, such as by using a Peltier cooler/vapor pressure control and mass flow controllers. The analyzer 26 compares the amount of elemental mercury received from the calibrator 28 with that of dry, substantially mercury-free gas (e.g., zero air), received from the gas supply 30 via conduit 44. The results of such a comparison allow direct calibration of the analyzer 26. A more detailed description of the calibrator 28 is provided below.

The system 20 monitors total mercury within a gas sample 32 in a substantially continuous manner. The converter 24, as used within the system 20, is configured to receive a gas sample 32, such as a gas sample 32 containing vaporized mercury, from the probe 22 and to separate oxidized mercury present within the gas sample 32 into an elemental mercury component and an oxidizing component. The converter 24 also operates to reduce the pressure of the gas sample 32 to minimize recombination of the elemental mercury component with the oxidizing components. The elemental mercury analyzer 26, as used within the system 20, is configured to receive the gas sample 32 from the converter 24, and detect the fluorescence of the elemental mercury within the sample. The elemental mercury analyzer 26 also utilizes a mechanism to reduce the effect of fluorescence quenching on the fluorescence of the elemental mercury within the sample 32. By reducing the effect of fluorescence quenching, the analyzer 26 provides substantially accurate measurement of the concentration of the elemental mercury in the gas sample 32.

Figure 2:
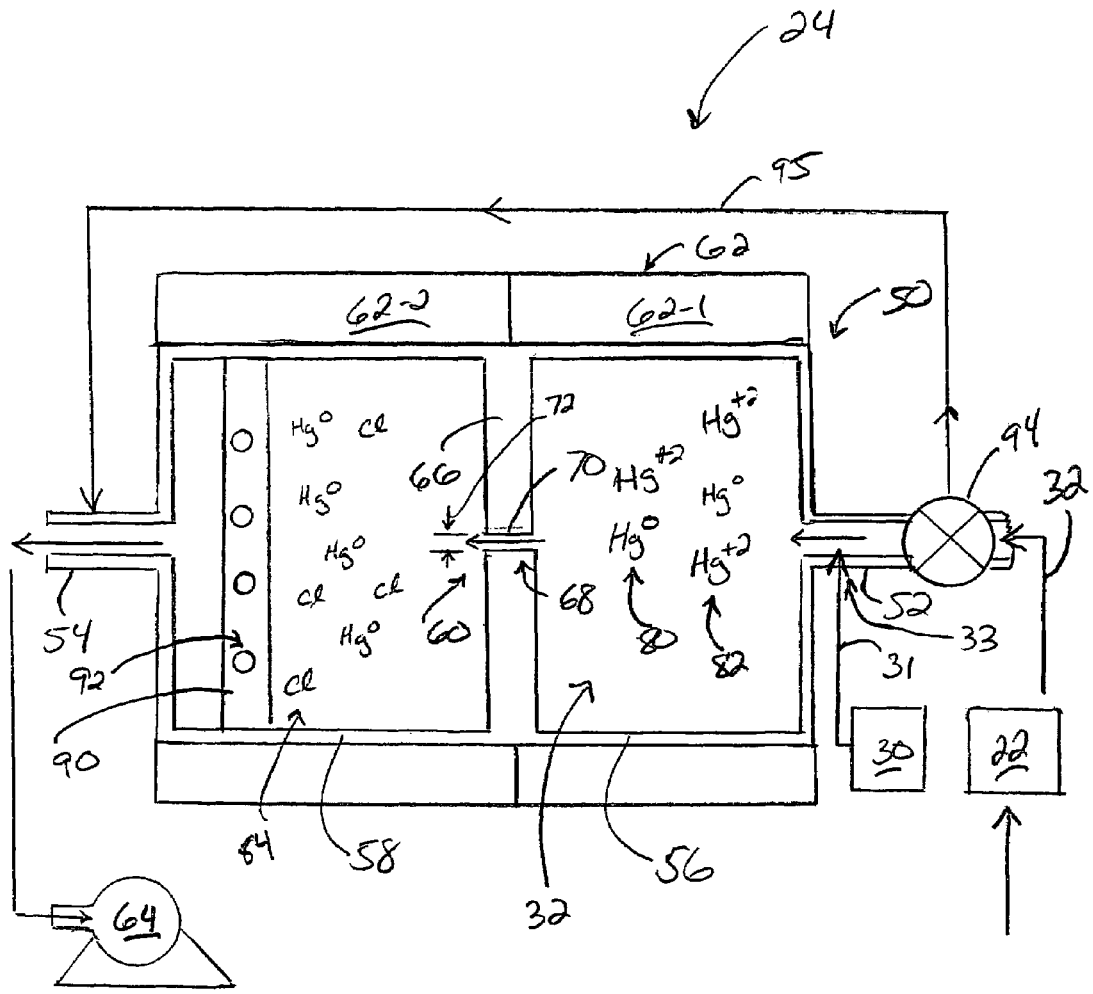
FIG. 2 illustrates an arrangement of an oxidized mercury converter according to one embodiment of the invention and which can be used with the mercury monitoring system of FIG. 1.

FIG. 2 illustrates an arrangement of the oxidized mercury converter 24. The converter 24 includes a housing 50 having an inlet 52, an outlet 54, and defining a first chamber 56 and a second chamber 58. The converter 26 also includes a pressure reduction apparatus 60 and a heater 62 in thermal communication with the housing 50.

The housing 50, in one arrangement, is a pyrolyzer formed from an alumina, quartz or glass material (e.g., high temperature quartz) into a generally cylindrical shape. The inlet 52 of the housing 50 is connected to a fluid or gas source for delivering a gas sample 32 from the fluid source to the first chamber 56 of the converter 24. For example, in one arrangement, the inlet 52 is connected to the probe 22 and receives a gas sample 32 from a stack or flue 34 of a coal combustion facility. The outlet 54 of the housing 50 is connected to the analyzer 26 illustrated in FIG. 1.

As shown in FIG. 2, in one arrangement, the outlet 54 communicates with a vacuum pump 64 which may in turn be connected to the inlet conduit 40 or outlet 42 of the analyzer 26 (e.g., the pump may be the analyzer pump). During operation, in one arrangement, the pump 64 draws the gas sample 32 into and through the probe 22, and through the converter 26 and the analyzer 26. In another arrangement, the converter 24 receives the gas sample 32 from a gas eductor associated with the probe 22. The pump 64, in such an arrangement, draws the gas sample 32 through the converter 26 and the analyzer 26.

The first chamber 56 of the converter 26 is configured to receive the gas sample 32 and contain the gas sample 32 substantially at a first pressure. For example, during operation, the pump 64 draws the gas sample 32 into the first chamber 56 from the probe 22 such that the first chamber 56 holds the gas sample at a pressure of approximately one atmosphere. The second chamber 58 is configured to receive the gas sample 32 from the first chamber 56 and contain the gas sample 32 substantially at a second pressure, the second pressure being less than the first pressure. As described below, the second chamber 58 operates in conjunction with the pump 64 and a pressure reduction apparatus 60 to contain the fluid or gas sample 32 at the second, decreased pressure.

The pressure reduction apparatus 60, together with the pump 64, establishes and maintains a reduced pressure of the gas sample 32 in the second chamber 58 relative to the pressure in the first chamber 56. To facilitate this, the pressure reduction apparatus 60 is, or includes, a flow restrictor 68 defining a channel or opening 70, such as a critical orifice, oriented between the first chamber 56 and the second chamber 58 of the housing 50. The flow restrictor 68 can be formed as a nozzle or a structure defining the orifice. In one arrangement, the flow restrictor 68 is formed within a wall 66 of the housing 50 which is common to the first chamber 56 and the second chamber 58—that is, separates the chambers 56, 58 one from another. The flow restrictor 68 creates a drop in the pressure of the gas sample 32, e.g., to between approximately 0.1 atmospheres and 0.3 atmospheres, as the pump 64 draws the gas sample 32 through the flow restrictor 68 from the first chamber 56 to the second chamber 58.

For example, during operation, the pump 64 draws the gas sample 32 from the inlet 52 into the first chamber 56. The first chamber 56 holds or contains the gas sample 32 at a first fluid pressure, such as at a pressure of one atmosphere (e.g., atmospheric pressure). The pump 64 further draws the gas sample 32 from the first chamber 56, through the flow restrictor 68, and into the second chamber 58. While the flow restrictor 68 allows flow of the gas sample 32 from the first chamber 56 to the second chamber 58, the flow restrictor 68 limits the flow rate of the gas sample 32 from the first chamber 56 to the second chamber 58. The size of the channel 70 of the flow restrictor 68 allows the pump 64 to create and maintain a low fluid pressure within the second chamber 58—between approximately 0.1 and 0.3 atmospheres, for example.

In one arrangement, a user can adjust a diameter 72 of the channel 70 of the flow restrictor 68 and a fluid flow rate of the pump 64 to achieve a pressure reduction of the gas sample to between approximately 0.1 and 0.3 atmospheres. For example, assume a case where the converter 24 has a flow restrictor 68 having a 500 milliliters/minute critical orifice (e.g., a diameter of approximately 0.001 inches) and the converter 24 couples to the pump 64 providing a vacuum flow rate of 500 milliliters/minute. During operation of the pump 64, the flow restrictor 68 reduces the pressure of the gas sample to between approximately 0.1 and 0.3 atmospheres.

The heater 62 is operable to heat the gas sample 32 within the housing 50 to convert or decompose oxidized mercury 82 present within the gas sample 32 into an elemental mercury component 80 and an oxidizing component 84. For example, the heater 62 can increase the temperature of the gas sample 32 within the first chamber 56 to approximately 750° Celsius (e.g., or within a range between approximately 650° C. and 800° C.). Such a temperature cracks the oxidized mercury 82 present within the gas sample 32 into an elemental mercury component 80 and an oxidizing component 84. In one arrangement, the heater 62 is an electrical resistance heater that provides radiant heat to the gas sample 32 within the housing 50.

During operation, the converter 26 receives a fluid sample 32 having oxidized mercury. For example, during operation, the probe 22 receives a flue gas sample 32 from a stack or flue 34 of a coal combustion facility. The gas sample 32 includes vaporized mercury in both elemental ($Hg^0$) 80 and oxidized ($Hg^{+2}$) 82 forms. The pump 64, coupled to the outlet 54 of the converter 26 (the pump 64 is preferably downstream of the analyzer 26), generates a vacuum within the housing 50 and causes the gas sample 32 to flow from the probe 22 to and through the converter 26. The first chamber 56 of the converter 26 receives the gas sample 32 and holds the sample 32 at a pressure such as approximately one atmosphere).

The converter 26 heats the fluid sample 32 having oxidized mercury to convert the oxidized mercury 82 present within the fluid sample 32 into an elemental mercury component 80 and an oxidizing component 84. For example, in a process known as thermal cracking, the heater 62 applies thermal energy to the first chamber 56 of the housing 50 to increase the temperature of the gas sample 32 within the first chamber 56 to temperature of approximately 750° C. As the oxidized mercury 82 within the gas sample 32 reaches the temperature of approximately 750° C., the oxidized mercury 82 converts into an elemental mercury component 80 and an oxidizing component 84, such as chlorine.

As the heated fluid sample passes through the flow restrictor, the converter 26 limits recombination of the elemental mercury component and the oxidizing component. For example, the vacuum pump and flow restrictor 68 can cause the pressure of the heated gas sample 32 to decrease from approximately 1 atmosphere (e.g., as contained within the first chamber 56) to between approximately 0.1 and 0.3 atmospheres (e.g., as contained within the second chamber 58). By reducing the pressure of the heated gas sample 32, relative to the pressure within the first chamber 56, the converter 24 reduces the number of elemental mercury components 80 and oxidizing components 84 within the second chamber 58. With the heated gas sample 32 held under a vacuum (e.g., held at a lower pressure relative to the pressure of the gas sample 32 within the first chamber 56), the reduced pressure or vacuum limits a recombination reaction between the converted elemental mercury 80 and oxidizing elements 84, as thermally converted within the first chamber 56. Additionally, the reduced pressure or vacuum limits the combination of the elemental mercury 80 within the gas sample 32 with other components, such as hydrochloric acid (HCl), which may be present within the gas sample 32.

As the heated gas sample 32 enters the second chamber 58 from the first chamber 56, and as it passes from the converter 54 towards the analyzer 26, the temperature of the heated gas sample 32 can decrease, thereby decreasing the probability for the elemental mercury 80 and oxidizing elements 84 present within the gas sample 32 to recombine. Reducing the pressure of the gas sample reduces the number of elemental mercury components 80 and oxidizing components 84 within the gas sample 32. Such reduction of the number of elemental mercury components 80 and oxidizing components 84 within the gas sample 32 reduces chemical recombination of the elemental mercury components 80 with the oxidizing components 84. Thus when the converter 24 delivers the gas sample 32 from the second chamber 58 to the analyzer 26, the analyzer 26 can detect, in a relatively accurate manner, the total amount of elemental mercury 80 (e.g., vaporized elemental mercury) within the gas sample 32.

As indicated above, in one arrangement, as the heated gas sample 32 enters the second chamber 58 from the first chamber 56, the temperature of the heated gas sample 32 decreases, thereby increasing the probability for the elemental mercury 80 and oxidizing elements 84 present within the gas sample 32 to recombine. To further minimize combination of the elemental mercury 80 and oxidizing elements 84 within the second chamber 58, the converter 24 can include a heater in thermal communication with the second chamber 58. Returning to FIG. 2, in one arrangement, the heater 62 includes a first heater portion 62-1 and a second heater portion 62-2. The first heater portion 62-1 is in thermal communication with the first chamber 56 and the second heater portion 62-2 is in thermal communication with the second chamber 58.

During operation, the first heater portion 62-1 heats the gas sample 32 within the first chamber 56, to a temperature of approximately 750° C., to crack the oxidized mercury 82 in the gas sample 32 into an elemental mercury component 80 and an oxidizing component 84. As the gas sample flows into the second chamber 58, the pressure reduction apparatus 60 (e.g., the flow restrictor 68) in combination with the pump 64 reduces the pressure of the gas sample 32 such that the gas sample is held at reduced pressure in the second chamber 58. The second heater portion 62-2 then applies heat to the second chamber 58 to help maintain the temperature of the gas sample 32 within the second chamber 58. For example, the second heater portion 62-2 also heats the gas sample 32 within the second chamber 58 to temperature of approximately 750° C. With such heating, the second heater portion 62-2 helps to maintain separation of the elemental mercury components 80 from the oxidizing components 84.

In certain cases, the gas sample 32 can require additional processing (e.g., removal of mercury reactive components) to limit oxidation of elemental mercury 80 within the gas sample 32 prior to its analysis. In one arrangement, to minimize recombination of decomposed elemental mercury components 80 and oxidizing components 84, the converter 24 includes a chemical scrubber 90, as illustrated in FIG. 2.

The chemical scrubber 90 acts to remove or reduce the presence of certain mercury reactive components within the gas sample 32. The chemical scrubber 90 can be mounted within the housing 50 downstream of flow restrictor 68 and upstream of the outlet 54 of the converter 24. Such orientation ensures that during operation the gas sample 32 flows through or in proximity to the chemical scrubber 90 as the gas sample 32 travels from the inlet 52 of the housing 50 to the outlet 54 of the housing 50, thereby allowing the chemical scrubber 90 to remove or reduce the presence of certain mercury reactive components within the gas sample 32. In one arrangement, the chemical scrubber 90 includes an acid gas scrubbing material 92, e.g., calcium hydroxide ($Ca(OH)_2$). The chemical or scrubber 92 traps certain components of the gas sample 32 (e.g., acid gases such as hydrochloric acid (HCl), and free chlorine radicals) to minimize combination of the acid gas components with elemental mercury 80 within the gas sample 32. That is, the chemical scrubber 90 permits elemental mercury ($Hg^0$) 80 to pass to the analyzer but removes acid gas components that could otherwise recombine with the elemental mercury 80.

Figure 7:
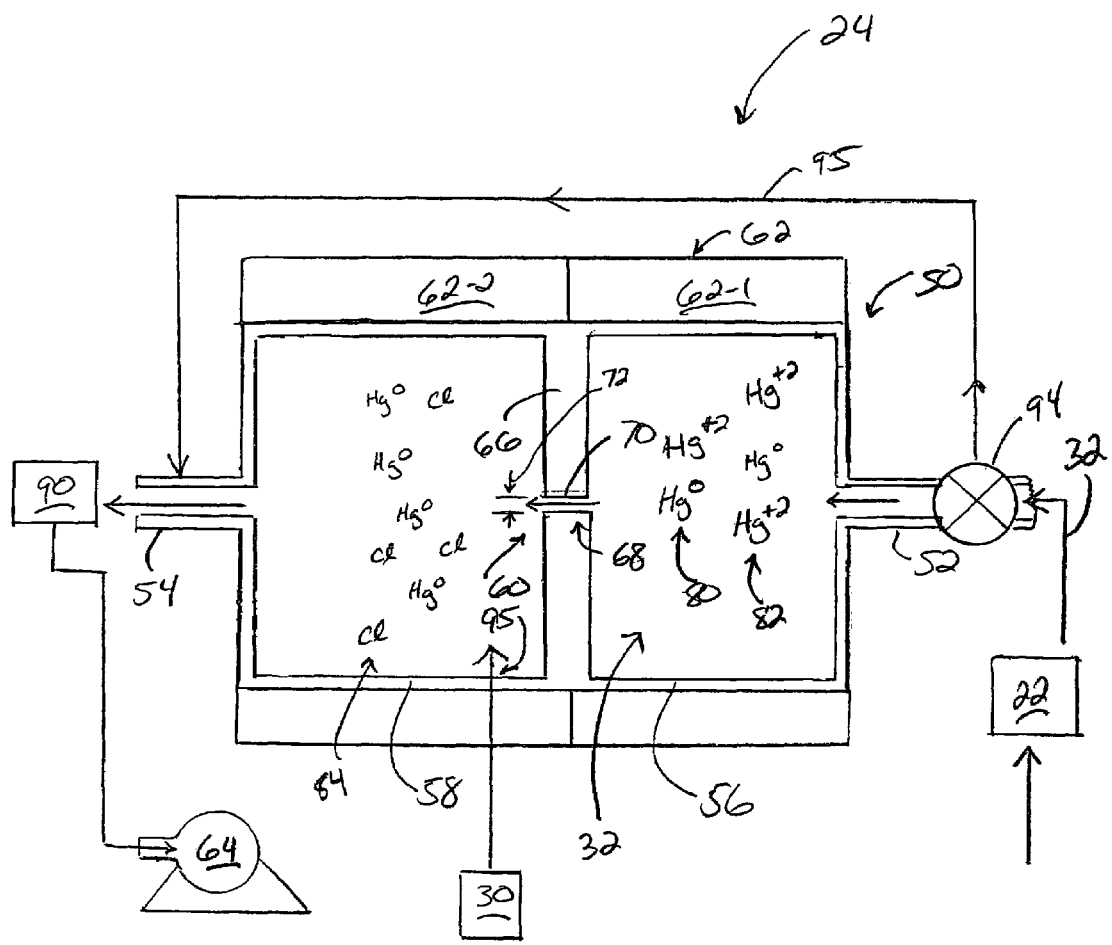
FIG. 7 illustrates an arrangement of the oxidized mercury converter of FIG. 2.

As an alternative to the arrangement shown in FIG. 2, a chemical scrubber can be provided within a separate housing downstream of the housing 50 (e.g., such as illustrated and described with respect to FIG. 7). Such an arrangement may facilitate replacement of the acid scrubbing material 92 (e.g., calcium hydroxide) of the chemical scrubber.

To further reduce or minimize the potential for recombination of elemental mercury into mercury-containing compounds, as in the second chamber 58 of the converter 24 or during the passage of a gas sample from the converter 24 to an analyzer 26, the gas supply 30 can provide dilution gas, such as dry mercury-free, non-oxidizing gas (e.g., nitrogen), into the sample stream via a conduit 31.

For example, as illustrated in FIG. 2, the dilution gas supply 30 provides mercury-free dilution gas to the converter 24. In one arrangement, the conduit 31 connects to a gas line of the system 20 upstream of the converter 24 near the inlet 52 of the converter 24. In another arrangement, the conduit 31 connects to a second inlet 33 of the housing 50. The dilution gas combines with the gas sample 32 to dilute the concentrations of oxidized mercury 82, elemental mercury 80 (e.g., vaporized mercury), and oxidizing components 84 within the gas sample 32 received by the converter 24. For example, the dilution gas supply 30 dilutes the oxidized mercury 82, elemental mercury 80, and oxidizing component 84 concentrations within the gas sample 32 at dilution ratios from between approximately 10:1 to 250:1. By diluting the amount of oxidized mercury 82, elemental mercury 80, and oxidizing components 84 present within the gas sample 32, the dilution gas supply 30 reduces the relative concentrations of the reactive species (e.g., the elemental mercury components 80 and the oxidizing components 84) within the gas sample 32.

The system 20 also can be operated to detect the concentration of elemental mercury of a gas sample 32 (e.g., from a combustion source) without requiring the system 20 to convert oxidized mercury present within the gas sample 32 into nonoxidized mercury (e.g., elemental mercury). To permit this, the system 20 includes a flow bypass element 94 (e.g., a valve) upstream of the converter 24 or connected to its inlet 52, as shown in FIG. 2. When activated, the flow bypass element 94 directs the gas sample 32, received by the inlet 52, through a conduit 95 and to the outlet 54 of the housing 50, thereby bypassing the first chamber 56 and the second chamber 58 of the housing 50. Such bypassing prevents the gas sample 32 from becoming exposed to a relatively high heat provided in the chambers 56, thus not cracking the oxidized mercury 82 present within the gas sample 32. This allows the analyzer 26 to detect only the elemental mercury originally present within the gas sample 32.

Figure 3:
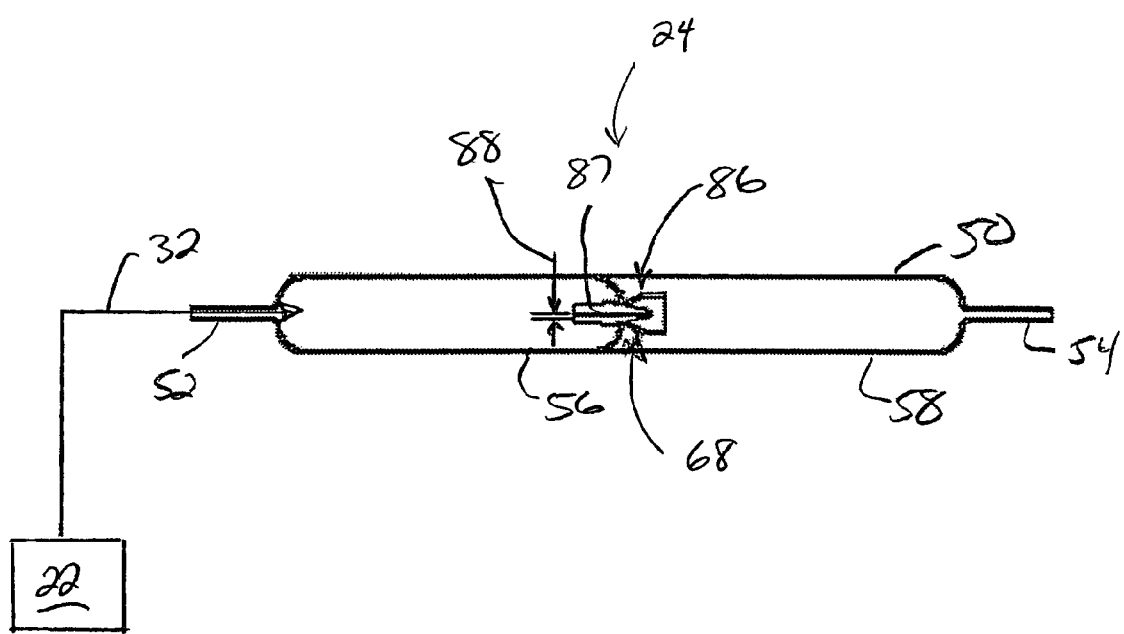
FIG. 3 illustrates an arrangement of the oxidized mercury converter of FIG. 2.
Figure 4:
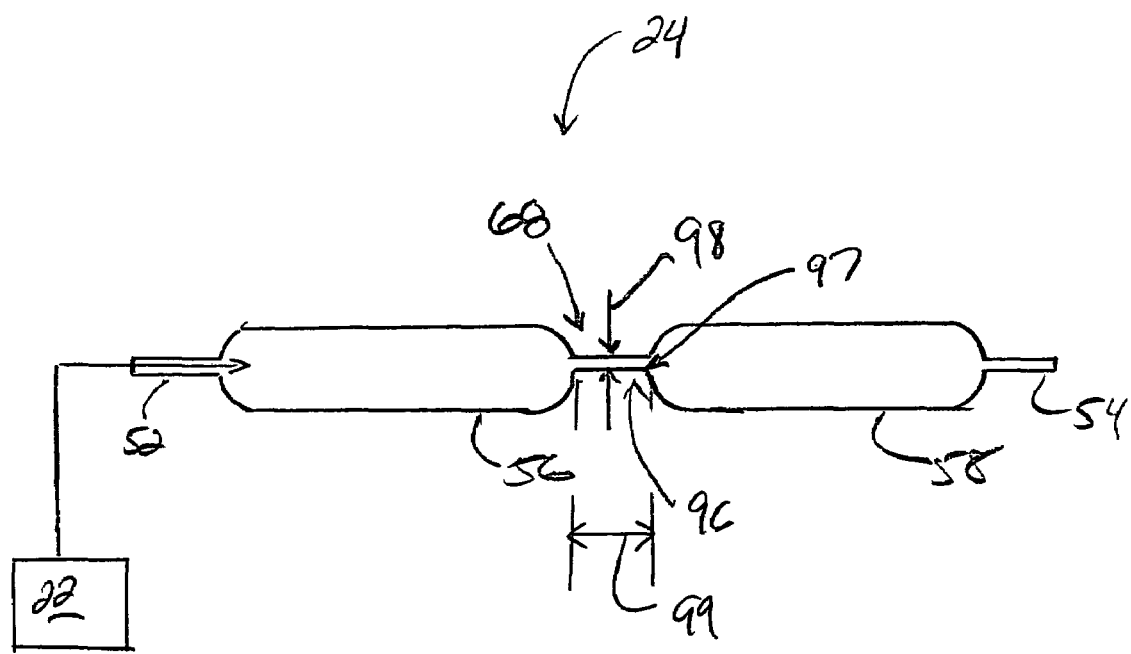
FIG. 4 illustrates an alternate arrangement of the oxidized mercury converter of FIG. 2.

As indicated above with respect to FIG. 2, the pressure reduction apparatus 60 (e.g., the flow restrictor 68 in combination with the pump 64) helps reduce the pressure of the gas sample 32 within the housing 50, relative to a pressure of the gas sample 32 received by the inlet 52. FIGS. 3 and 4 illustrate alternate configurations for the pressure reduction apparatus 60.

FIG. 3 illustrates a flow restrictor 68 configured as a nozzle 86 between the first chamber 56 and the second chamber 58 of a converter 26. The nozzle 86 defines a channel or orifice 87 having a diameter 88 that limits flow rate of the gas sample 32 from the first chamber 56 to the second chamber 58. The use of a separately attachable flow restrictor 68 (e.g., the nozzle 86) allows installation of different flow restrictors 68 having varying diameters to achieve different desired flow rates.

FIG. 4 illustrates another arrangement of a flow restrictor 68 for a converter 24. As shown, the flow restrictor 68 is a neck portion 96 integrally formed with the housing 50 and connecting the first chamber 56 to the second chamber 58. The neck portion 96 separates the first chamber 56 from the second chamber 58 by a distance 99. The neck portion 96 defines a channel or orifice 97 having a diameter 98 which allows flow of the gas sample 32 from the first chamber 56 to the second chamber 58 and that limits a flow rate of the gas sample 32 from the first chamber 56 to the second chamber 58. For example, in one arrangement, the orifice 97 of the neck portion 96 permits a maximum flow rate of approximately 500 milliliters/minute. The integral arrangement shown in FIG. 4 allows manufacture of the first chamber 56, the second chamber 58, and the neck portion 96 in a single manufacturing procedure from a single material (e.g., high temperature quartz), eliminating steps needed to install a separate pressure reduction apparatus within the housing 50.

Figure 5:
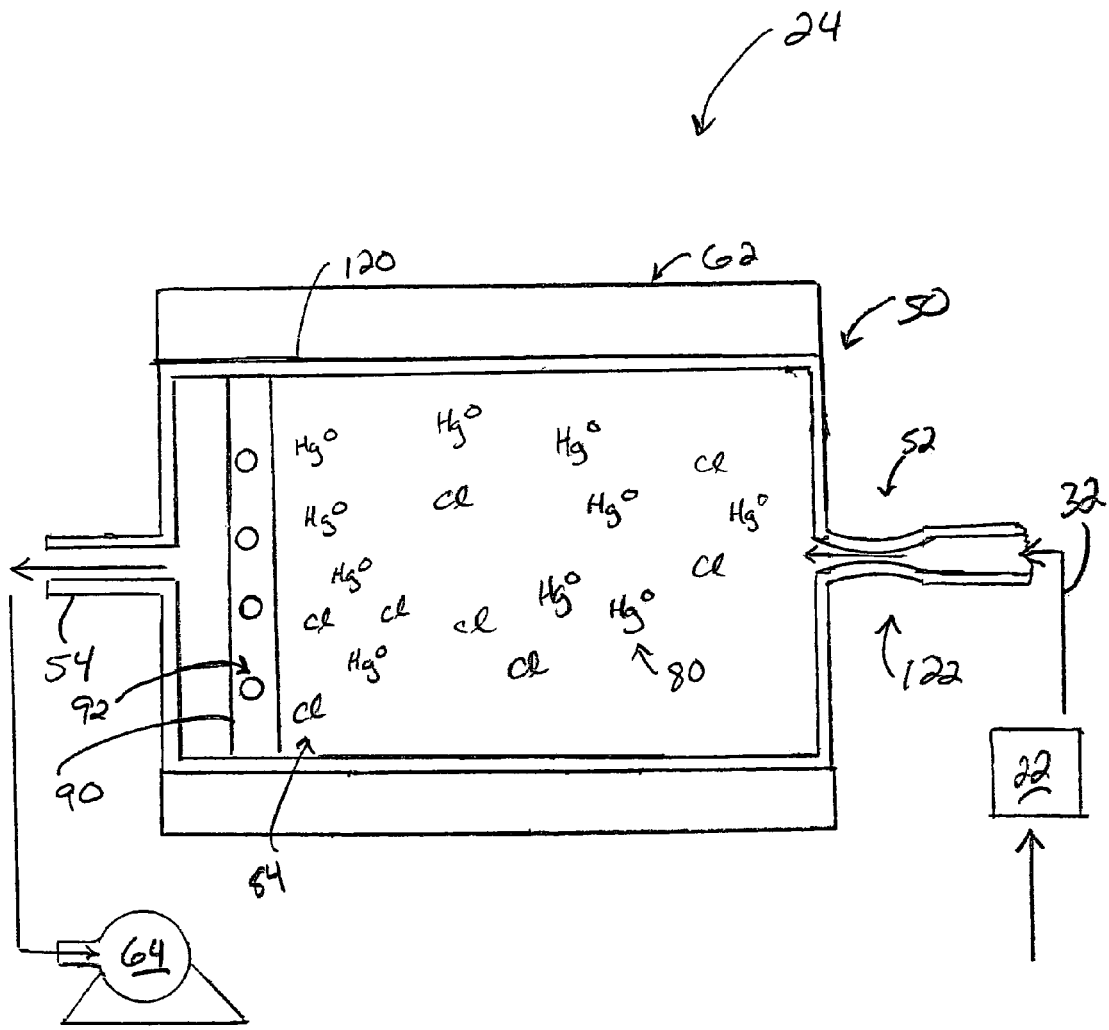
FIG. 5 illustrates another arrangement of an oxidized mercury converter according to one embodiment of the invention and which can be used with the mercury monitoring system of FIG. 1.

FIG. 5 illustrates an alternate arrangement of the converter 24 where the converter 24 defines a single chamber 120 and includes a flow restrictor 122 located upstream (e.g., at the inlet 52) of the converter 24. The flow restrictor 122, in combination with the pump 64 (e.g., as connected to the outlet 42 of the analyzer 26 (not shown)), reduces the pressure of the gas sample 32 as the gas sample 32 enters the chamber 120. During operation, the flow restrictor 122, in combination with the pump 64, reduces the pressure of the gas sample 32 from atmospheric pressure to between approximately 0.1 and 0.3 atmospheres. As the converter 24 receives the reduced pressure gas sample 32, the heater 62 applies heat to the gas sample 32 to thermally crack the oxidized mercury within the reduced pressure gas sample 32. The single chamber 120 maintains the gas sample at the reduced pressure. With the flow restrictor 122 located upstream to the converter 24, the converter 24 maintains the reduced pressure of the gas sample 32 to reduce or limit recombination of the elemental mercury components 80 and the oxidizing components 84.

Figure 6:
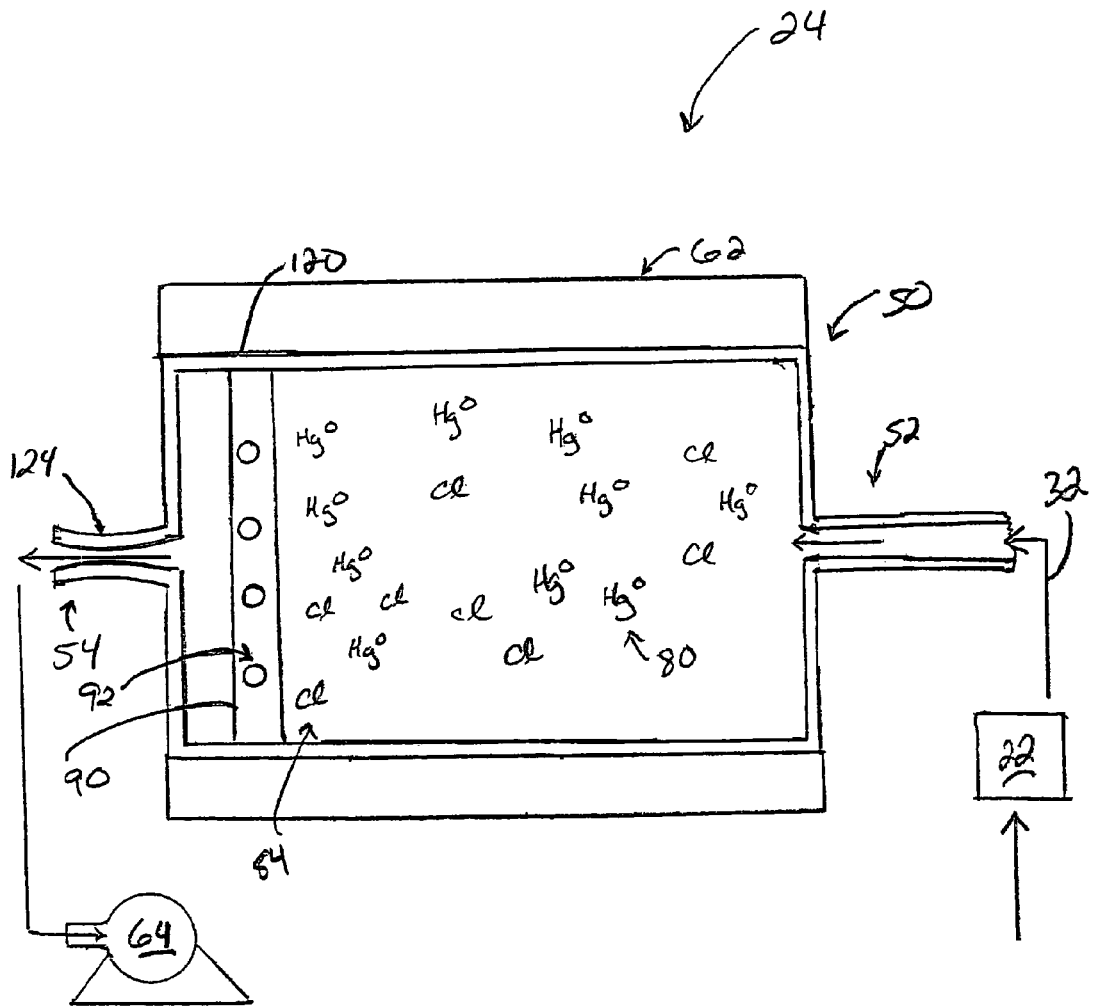
FIG. 6 illustrates an arrangement of the oxidized mercury converter of FIG. 5.

FIG. 6 illustrates an alternate arrangement of the converter 24 where the converter 24 defines the single chamber 120 and includes a flow restrictor 124 located at the downstream end (e.g., at, or as part of, the outlet 54) of the converter 24. The flow restrictor 124, in combination with the pump 64, reduces the pressure of the gas sample 32 as the gas sample 32 exits the chamber 120. During operation, the converter 24 receives the gas sample 32 within the single chamber 120 and the heater 62 applies heat to the gas sample 32 to thermally crack the oxidized mercury within the gas sample 32. As the gas sample 32 exits the single chamber 120, the flow restrictor 124, in combination with the pump 64, reduces the pressure of the gas sample 32 from atmospheric pressure to between approximately 0.1 and 0.3 atmospheres. With the flow restrictor 124 located at the downstream end of the converter 24 (the flow restrictor can alternatively be a structure separate from the converter 24 and positioned between the converter 24 and the analyzer 26), the converter 24 delivers a reduced pressure gas sample 32 to the analyzer 26 within the system 20. By reducing the pressure of the thermally cracked gas sample 32, the converter 24 reduces or limits recombination of the elemental mercury components 80 and the oxidizing components 84 within the gas sample as the gas sample travels to the analyzer 26.

Also as indicated above and as illustrated in FIG. 2, the dilution gas supply 30 provides a dilution gas to a flow line upstream of the converter 24. In an alternative arrangement, as shown in FIG. 7, the dilution gas supply 30 may introduce dilution gas into the second chamber 58 of the housing 50 of the converter 24 by way of a second inlet 95 associated with the housing 50. By diluting the oxidized mercury 82, elemental mercury 80, and oxidizing components 84 present within the gas sample 32 within the second chamber 58, the dilution gas supply 30 reduces the relative concentrations of the reacting species (e.g., the elemental mercury components 80 and the oxidizing components 84) within the gas sample 32 (i.e., within the second chamber 58).

As illustrated in FIG. 2, the chemical scrubber 90 is located within the housing 50 of the converter 24. In another arrangement, as illustrated in FIG. 7, the chemical scrubber 90 is located external to the housing 50 of the converter 24. Such an arrangement allows a user to easily change or replace the particle collection portion 92 (e.g., calcium hydroxide) of the scrubber 90. While the external scrubber 90 is illustrated as being located downstream from the outlet 54, the external scrubber 90 can also be located at an upstream location, in proximity to the inlet 52.

As indicated above, the system 20 monitors total mercury within a gas sample 32 in a substantially continuous manner. After the converter 24 converts the oxidized mercury present within the gas sample 32 into elemental mercury and reduces the pressure of the gas sample to minimize recombination of the elemental mercury with the oxidizing elements present within the gas sample 32, the gas sample 32 flows to the analyzer 26. The analyzer 26 then detects the total mount of mercury present within the gas sample 32.

Figure 8:
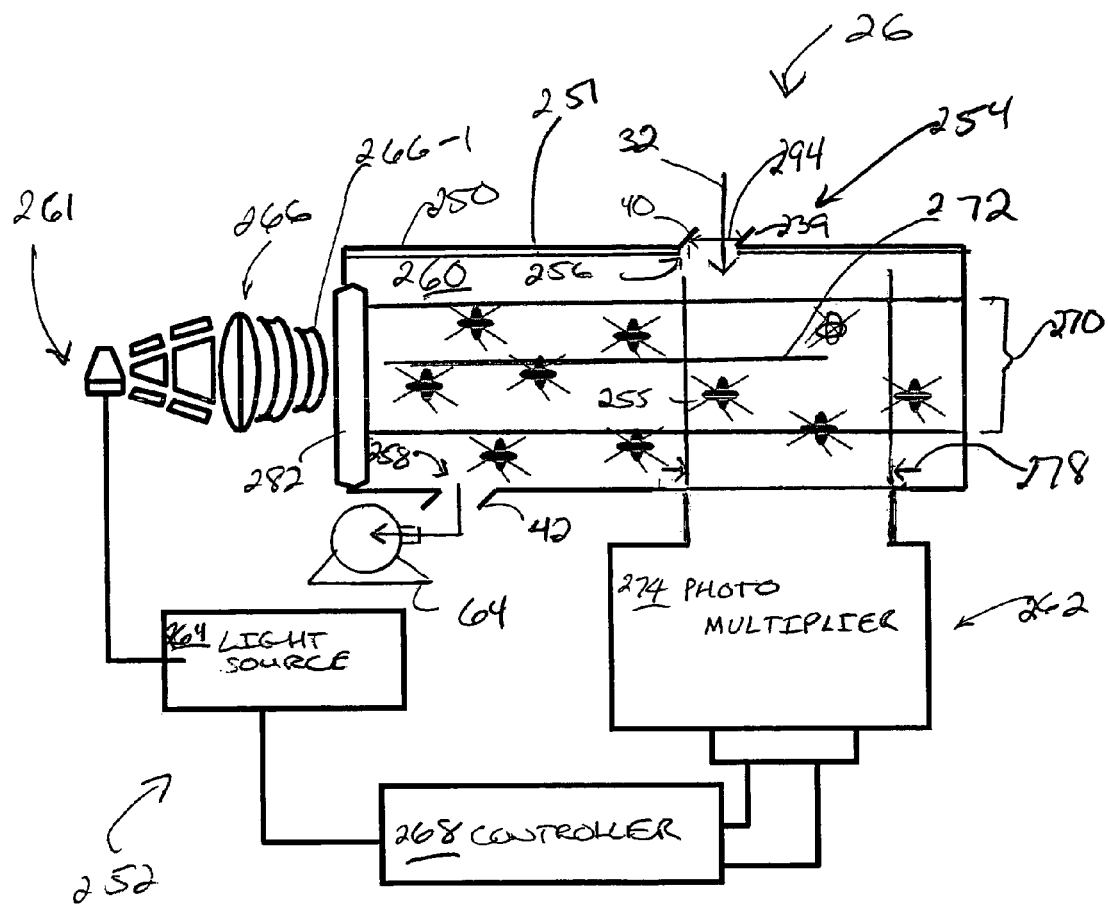
FIG. 8 illustrates an arrangement of a mercury analyzer as used within the mercury monitoring system of FIG. 1.

FIG. 8 illustrates an arrangement of the elemental mercury analyzer 26. The analyzer 26 includes a housing 250, and a fluorescence assembly 252.

The housing 250 has an inlet 256, an outlet 258, and defines a chamber 260. The inlet 256 is configured to receive the reduced pressure gas sample 32 (e.g., the gas sample 32 having a pressure between 0.1 and 0.3 atmospheres) from the converter 24 via the conduit 40. The outlet 258 is configured to discharge or exhaust the fluid or gas sample 32 to the atmosphere via the exhaust port 242. The chamber 260 is configured to contain the gas sample 32, such as a gas emissions sample, during analysis of the sample. In one arrangement, light baffling material 251 is included within the chamber 260 to minimize scattering of light within the chamber 260.

The fluorescence assembly 252 includes a light source assembly 261 and a detector assembly 262 in optical communication with the chamber 260 and hence with a gas sample 32 contained by the housing 250. The fluorescence assembly 522 induces fluorescence of elemental mercury 255 present within the gas sample 32 and detects a fluorescence signal of the gas sample 32 based upon fluorescence of the elemental mercury.

The light source assembly 261, in one arrangement, includes a light source 264 and lenses 266. The light source 264, in one arrangement, is a high-intensity mercury lamp which produces light at a wavelength of approximately 253.7 nm and delivers the light to the lenses 266. The lenses 266, in turn, direct the light from the light source 264 to the chamber 260. As the lenses 66 direct the light from the light source 264 into the chamber 260, the light (e.g., having the wavelength of approximately 253.7 nm) excites elemental mercury 255 located within the chamber 260. As a result of the excitation, the elemental mercury 255 releases energy, such as via fluorescence.

The detector assembly 262, in one arrangement, includes a photo multiplier tube 274 electrically coupled to the controller 268. The photo multiplier tube 274 is in optical communication with the chamber 260 of the housing 250 and is operable to receive and detect light fluoresced by the elemental mercury 255 within the chamber 260. As the photo multiplier 274 receives a fluorescence signal from the fluid sample (e.g., fluoresced light from the elemental mercury 255), the photo multiplier 274 generates a signal proportional to the fluorescence signal (e.g., proportional to the intensity of the fluorescence of the elemental mercury 255 within the gas sample 32) and transmits the signal to the controller 268. The controller 268 (e.g., its memory and processor) calculates or detects the concentration of the elemental mercury 255 in the gas sample 32 based upon the signal received from the photo multiplier 274.

In one arrangement, the analyzer 26 utilizes a polarizing element in conjunction with the light source assembly 261 and the detector assembly 262 to improve detection of the signal of the fluoresced light from the elemental mercury 255 and, ultimately, the signal-to-noise ratio of the detector assembly 262.

For example, the light source assembly 261 includes a polarizing element or filter 282 positioned between the lenses 266 and the chamber 260 of the housing 250. The polarizing filter 282 polarizes the incident light from the lenses 266 to reduce an amount of scattered light observed by the detector. The polarizing filter 282 is oriented to pass only the plane of light orthogonal to the plane of light transmitted by light scattering thereby reducing the amount of scattered light within the chamber 260.

During operation, the polarizing filter 282 polarizes incident light entering the chamber 260 to remove the plane of light transmitted by light scattering. As the polarized incident light travels through the chamber 260, the polarized light can become scattered (e.g., as caused by interaction between the polarized light and the walls of the housing 250 or particulate matter in the gas sample 32 contained by the housing 250). The light scatter resulting from particle interaction favors one of two orthogonal planes, depending on the orientation of the polarizing element 282 and the detector 262. By transmitting only an unfavorable plane of light (e.g., the plane of light orthogonal to the plane of light transmitted by light scattering) into the fluorescing chamber 260, the amount of scattered light is reduced within the chamber 260. A reduction in scattered light enhances the detector's 262 ability to monitor mercury. The elemental mercury 55 fluoresces light as non-polarized light. Therefore, the use of polarized light improves detection of the signal of the fluoresced light from the elemental mercury 255 and provides the detector assembly 262 with an enhanced or improved fluorescence detection limit.

As indicated above, when polarized incident light travels through the chamber 260, the polarized light can become scattered. Typically, scattered light observed at a right angle to the direction of propagation of the polarized incident light is plane polarized.

In one arrangement, the polarizing filter 282 of the light source assembly 261 directs polarized incident light along a first axis or optical orientation 272 within the chamber 260. For example, the first optical orientation 272 is substantially perpendicular (e.g., at a substantially 90 degree angle) to a face of the polarizing filter 282 while the scattered light is substantially parallel to the face of the polarizing filter 282.

During operation, polarized incident light traveling along the first optical orientation 272 causes elemental mercury 255 present within a first optical zone 270 to fluoresce. When polarized light travels or propagates within the chamber 260 along the first optical orientation 272, the polarized light can scatter within the chamber 260. As stated above, scattered light detected at a right angle to the direction of propagation of the polarized incident light has a linear polarization. Therefore, the detector 262 detects fluoresced light within a second optical zone 278 of the chamber 260 where the second optical zone 278 is oriented at a substantially 90 degree angle relative to the first optical zone 270. The orientation of the detector 262 relative to the plane of scattered light optimizes detection of the fluorescence signal from the gas sample. Additionally, removing what would otherwise be the favorable scattering plane of light from the source reduces the scattered light resulting from particle interaction.

Collisional deactivation can cause fluorescence quenching of elemental mercury within a fluid or gas sample. In the process of collisional deactivation, an excited mercury atom collides with another atom/molecule within the gas sample or with a wall of the analyzer 26 and transfers energy with the object of the collision without emitting light—i.e., the excited elemental mercury atom surrenders its energy through a non-fluorescent mechanism. However, the analyzer 26 of the present mercury monitoring system receives from the converter 24 a gas sample 32 having a relatively low pressure, e.g., between approximately 0.1 atmospheres and 0.3 atmospheres, and maintains the gas sample 32 at the relatively low pressure. By receiving and maintaining the gas sample 32 at a relatively low pressure (e.g., with a reduced number of atoms (mercury atoms) within the chamber 60), the analyzer 26 reduces the number of atomic/molecular interactions of the excited mercury atoms within the chamber 260. Hence the analyzer 26 reduces the effect of collisional deactivation and, therefore, fluorescence quenching on the fluorescence of the elemental mercury 255.

The quenching of mercury fluorescence follows the classical Stern-Volmer equation when mercury concentrations are sufficiently low. This condition is met in the present analyzer 26 for detection of trace levels of mercury. For a gas sample 32 containing a constant fraction, or mixing ratio, of mercury diluted in another gas, the fluorescence intensity changes with pressure according to the following equation:

$$F(M, p) = C \cdot (p/(1+\phi_M p))$$

where $F(M, p)$=Fluorescence intensity of mercury in mixing gas M at pressure p
  C=Constant depending on the mixing ratio
  p=Sample pressure
  $\phi_M$=Quenching coefficient for mixing gas M The relative fluorescence intensity of mercury in the gas sample, compared to a gas sample at 1 atmosphere absolute pressure is calculated from:

$$F(M, p)/F(M_{Ref}, 1 \text{ atm}) = (p \cdot (1+\phi_{MRef}))/(1+\phi_M p)$$

where $M_{Ref}$=Reference mixing gas.

In the case where the reference mixing gas is air, the quenching coefficient for air is $\phi_{Air}$=140/atmosphere. In the case where the reference mixing gas is nitrogen the quenching coefficient for nitrogen is, $\phi_{Nitrogen}$=18/atmosphere.

Figure 9:
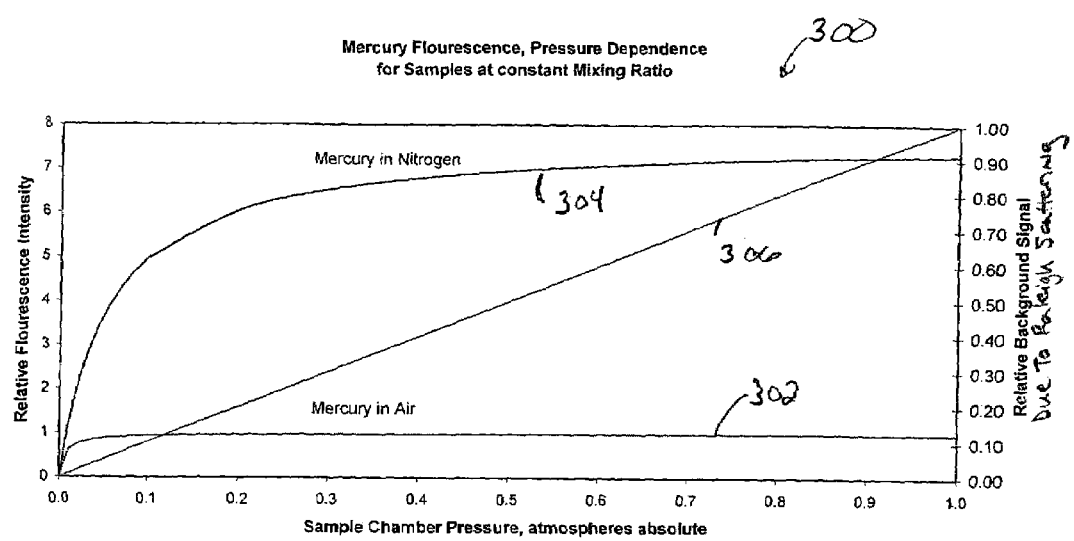
FIG. 9 illustrates relationships between relative fluorescence intensity and sample chamber pressure.

FIG. 9 is a graph 300 that illustrates relationships (e.g., the Stem—Volmer relationship) between relative fluorescence intensity and sample chamber pressure (e.g., sample chamber pressure relative to a reference of air at 1 atmosphere pressure) for mixtures of mercury in air and mercury in nitrogen.

A first curve 302 represents a relationship between relative fluorescence intensity and sample chamber pressure for a gas sample 32 with mixtures of mercury in air. A second curve 304 represents a relationship between relative fluorescence intensity and sample chamber pressure for a gas sample 32 with mixtures of mercury in nitrogen.

FIG. 9 shows that for mercury in air (represented as the first curve 302), the high or upper pressure limit is reached at approximately 0.1 atmospheres. Above this pressure, the effect of an increase in the number of absorbing mercury atoms with increasing pressure is cancelled by an equivalent increase in the rate of quenching of the increased number of excited state mercury atoms which are produced. As a consequence, little increase in fluorescence signal can be obtained by increasing the air sample pressure beyond 0.1 atmospheres. Conversely, little fluorescence signal is lost by operating the analyzer sample chamber 260 under a partial vacuum and reducing the sample pressure from atmospheric pressure to 0.1 atmospheres absolute pressure.

The graph 300 shows that the sample pressure for mixtures in air can be reduced to 0.1 atmospheres without significant reduction in fluorescence intensity. The graph 300 also includes a third curve 106 that represents a relationship between relative background signal caused by scattering of light by air/nitrogen molecules and sample chamber pressure. As shown, the scattering of excitation energy by the air/nitrogen molecules (e.g., Raleigh scattering) is reduced proportionally relative to a reduction in pressure. For example, at a pressure of 0.1 atmospheres, the relative background signal is reduced to approximately $\frac{1}{10}$ of the value at 1 atmosphere pressure. That is, a reduction in pressure within the chamber 260 has the effect of greatly reducing the background signal, which is present even when there is no mercury in the sample gas. The reduced intensity of background signal or light allows for the detection of relatively low levels of mercury vapor, thereby enhancing the Lower Detectable Limit (LDL) of the mercury monitoring system 20.

FIG. 9 also shows the effect of diluting the sample with nitrogen rather than air, as indicated by the second curve 304. At an operating pressure of 0.1 atmospheres, for example, the fluorescence intensity is increased by approximately a factor of five. This increase occurs with little change in the scattered light intensity. The background intensity is thus reduced five fold compared to the fluorescence signal, yielding a further improvement in the LDL for mercury.

During operation, the analyzer 26 receives a reduced pressure gas sample 32 from the converter 24. For example, in one arrangement, the converter 24 reduces the pressure of the gas sample 32, such as received from a stack or flue 34 of a coal combustion facility, from a pressure of about 1 atmosphere to between 0.1 and 0.3 atmospheres. The analyzer 26 then induces fluorescence of elemental mercury present within the reduced pressure gas sample 32. For example, the light source assembly 61 of the analyzer 26 produces light at a wavelength of approximately 253.7 nm to induce fluorescence of elemental mercury within the gas sample 32.

The analyzer 26 detects a fluorescence signal of the gas sample 32 based upon fluorescence of the elemental mercury 255 within the gas sample 32, the fluorescence signal proportional to a concentration of elemental mercury 255 within the gas sample 32. For example, the detector assembly 262 of the analyzer 26 receives a fluorescence signal from gas sample 32 as generated by fluorescing of elemental mercury 255 within gas sample. Based upon the fluorescence signal, the detector assembly 262 calculates a concentration level for the fluid sample and provides an output, such as to a user or operator.

The analyzer 26 performs the method over real-time in a substantially continuous manner. For example, the analyzer detects the elemental mercury concentration of a gas sample at a particular rate (e.g., once every second) and provides the concentration result as an output from the analyzer at the particular rate. As a gas sample 32 flows into the analyzer 26 at a substantially continuous rate, the analyzer 26 performs the real time mercury concentration analysis of the gas sample 32. Thus the analyzer 26 can detect "spikes" in the concentration of elemental mercury 255 present within the fluid sample or trends (e.g., an increase or decrease) relating to the mercury concentrations within the sample over time.

As indicated above, with the analyzer 26 (e.g., via the pressure reduction apparatus) receiving and containing the gas sample 32 from the converter 24 at a relatively low pressure (e.g., between 0.1 and 0.3 atmospheres) the analyzer 26 causes the number of molecular collision of the elemental mercury 255 to drop. However, the number of excited elemental mercury atoms available to fluoresce is proportional to the pressure. Therefore, a pressure reduction of the gas sample 32 also reduces the number of excited elemental mercury atoms available to fluoresce. By containing the gas sample 32 under a vacuum or negative gage pressure, the analyzer 26 reduces the fluorescence intensity or signal produced by the excited elemental mercury 255 within the fluid sample 32 during fluorescence of the excited elemental mercury 255. However, while the effect of reduced pressure on the gas sample 32 places greater demands on detection sensitivity, fluorescence detection according to the invention provides a substantially sensitive and accurate method for detecting the concentration of elemental mercury within a fluid sample.

As indicated above, the analyzer 26 receives, from the converter 24, a gas sample 32 having a relatively low pressure, between approximately 0.1 atmospheres and 0.3 atmospheres, and maintains the gas sample 32 at the relatively low pressure. The analyzer 26 reduces the effect of collisional deactivation and, therefore, fluorescence quenching on the fluorescence of the elemental mercury 255. However, in certain cases, the analyzer 26 can receive the gas sample 32 from the converter 24 at a pressure greater than approximately 0.3 atmospheres. In order to reduce the number of atomic/molecular interactions of the excited mercury atoms within the chamber 260 to reduce the effect of collisional deactivation fluorescence quenching on the fluorescence of the elemental mercury 255, the analyzer 26 includes a fluorescence quenching reduction mechanism. The fluorescence quenching reduction mechanism is configured to reduce the effect of fluorescence quenching on the fluorescence of the elemental mercury 255 within the sample 32.

Returning to FIG. 8, in one arrangement, the fluorescence quenching reduction mechanism includes a pressure reduction apparatus 254 coupled to the housing 250 (e.g., in the case where the analyzer 26 receives the gas sample 32 from the converter 24 at a pressure greater than approximately 0.3 atmospheres). The pressure reduction apparatus 254 reduces the pressure of the gas sample 32 relative to that of a fluid source, such as the stack or flue 34 of a coal combustion facility or converter 24 as illustrated in FIG. 1, to minimize or reduce fluorescence quenching of the elemental mercury 255 within the gas sample 32.

With reference to FIG. 8, in one arrangement, the pressure reduction apparatus 254 includes the vacuum pump 64 operating in conjunction with a flow restrictor 239 of the housing 250. As illustrated, the outlet 258 of the housing 250 is in fluid communication with the vacuum pump 64. The inlet 256 of the housing is configured as, or includes, a flow restrictor 239

(e.g., a nozzle) that defines a relatively narrow width or diameter 294, relative to a width or diameter of the heated conduit 40. During operation, for example, the vacuum pump 64 draws the fluid sample 32 from the converter 24, and into the housing 250 of the analyzer 26 through the flow restrictor 239 of the housing 250. As the gas sample 32 flows through the flow restrictor 239 (e.g., the flow restrictor of the inlet 256), the pressure of the gas sample 32 decreases from a first pressure, such as a pressure of approximately 1 atmosphere as contained within the converter 24 to a second pressure between approximately 0.1 and 0.3 atmospheres (e.g., as contained within the analyzer 26).

Figure 10:
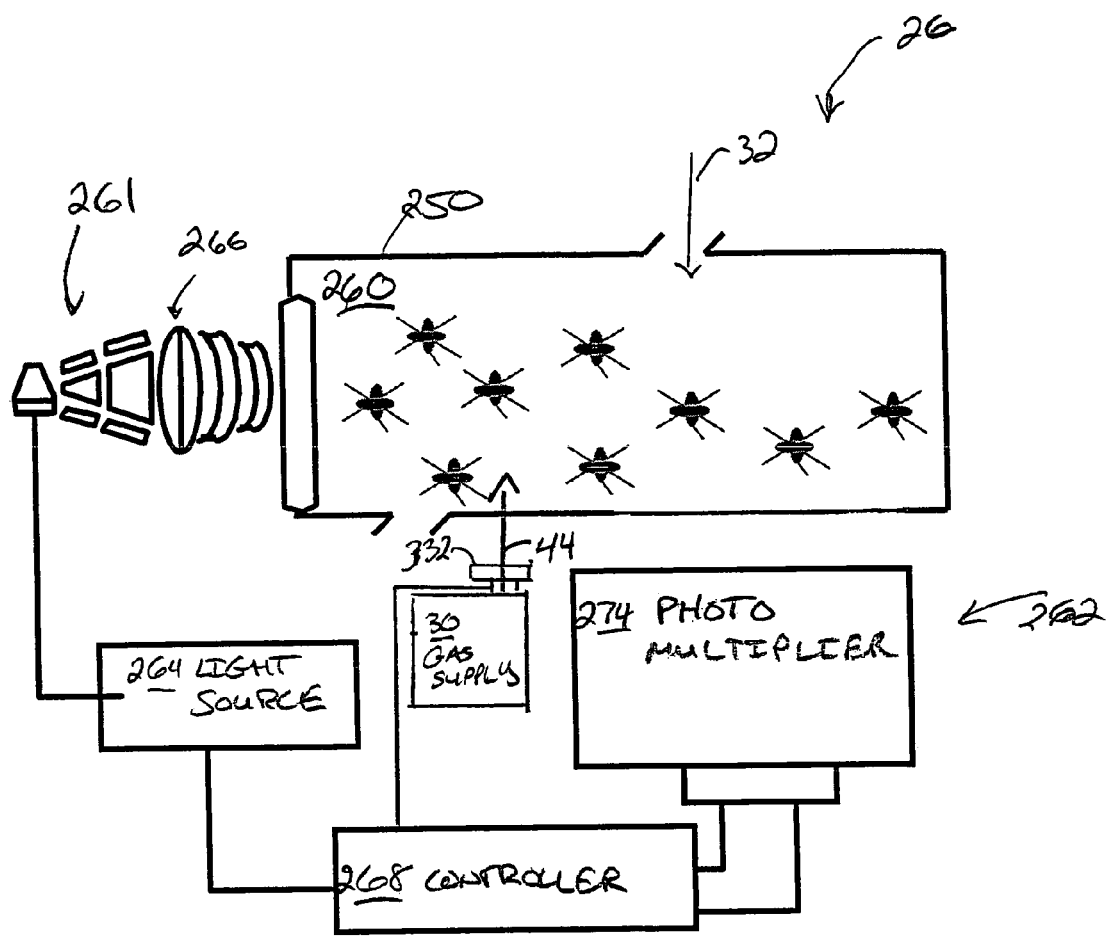
FIG. 10 illustrates an arrangement of a mercury analyzer as used within the mercury monitoring system of FIG. 1.

FIG. 10 illustrates another arrangement of the analyzer 26. As illustrated, the fluorescence quenching reduction mechanism 254 of the analyzer 26 is configured as the gas supply 30 (e.g., an oxygen depleted gas source) containing oxygen depleted gas, such as pure nitrogen gas. In one arrangement, the oxygen depleted gas source 30 delivers the oxygen depleted gas to the chamber 260 of the analyzer 26 via the conduit 44. In another arrangement, the oxygen depleted gas source 30 delivers the oxygen depleted gas to the probe 22 via the conduit 47 (e.g., as indicated in FIG. 1). Oxygen depleted gases, such as pure nitrogen gas, quench the fluorescence of elemental mercury significantly less than oxygen. Introduction of an oxygen depleted gas into the chamber 260 dilutes the fluid sample 32 and reduces fluorescence quenching of elemental mercury within the gas sample 32. Also, introduction of an oxygen depleted gas into the probe 22 dilutes the fluid sample 32 and reduces fluorescence quenching of elemental mercury within the gas sample 32.

In one arrangement, a valve assembly 332 is positioned between the oxygen depleted gas source 30 and the housing 250 to regulate the amount of oxygen depleted gas delivered from the source, and the valve assembly 332 is electrically coupled to the controller 268. The controller 268 regulates opening and closing of the valve assembly 332 to control the amount of oxygen depleted gas delivered to the chamber 260 or to the probe 22.

Figure 11:
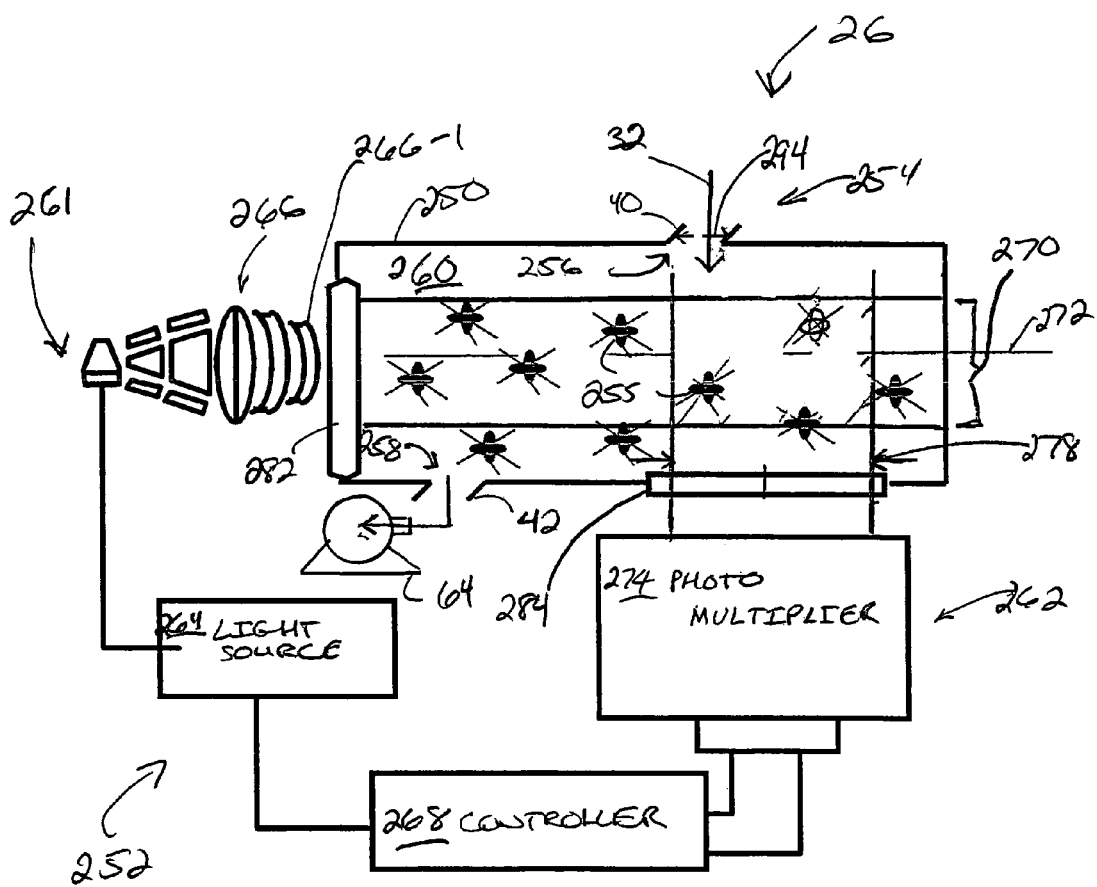
FIG. 11 illustrates another arrangement of a mercury analyzer as used within the mercury monitoring system of FIG. 1.

In one arrangement, as illustrated in FIG. 11, the analyzer 26 includes a first polarizing filter 282 and a second polarizing filter 286 where the polarizing filters 282, 284 are crossed relative to each other and relative to a favored scattering plane. As indicated above, the use of a single polarizing filter 282 reduces the effect of light scattering within the chamber 260 as caused by interaction of the light with the gas within the chamber 260. The use of crossed polarizing filters 282, 284 minimize the effect of other types of optical interferences formed within the analyzer 26. For example, the crossed polarizing filters 282, 284 minimize the effects of light reflected from the walls of the chamber on the output signal (e.g., fluorescence) detected by the detector assembly 262.

As indicated above, the analyzer 26 requires periodic calibration in order to accurately detect or measure the presence of elemental mercury within a gas sample 32. As illustrated by FIG. 1, calibration is provided by the calibrator 28 which, in one arrangement is in fluid communication with the analyzer 26 through a line or conduit 45 and provides vaporized elemental mercury to the analyzer 26 at a particular concentration, such as by using a Peltier cooler/vapor pressure control and mass flow controllers. The analyzer 26 compares the amount of elemental mercury received from the calibrator 28 with that of dry, substantially mercury-free gas, received from the gas supply 30 via conduit 44. The results of such a comparison allow direct calibration of the analyzer 26.

In certain cases, the analyzer 26 requires periodic calibration in order to accurately detect or measure the presence of both elemental and oxidized mercury within a gas sample 32. The calibrator 28 is connected to the converter 24 and provides a known concentration of oxidized mercury, such as in the form of a mercury-containing vapor, to the converter 24. By providing oxidized mercury having a known concentration, the calibrator 28 allows calibration of the analyzer 26 within the mercury monitoring system 20.

Figure 12:
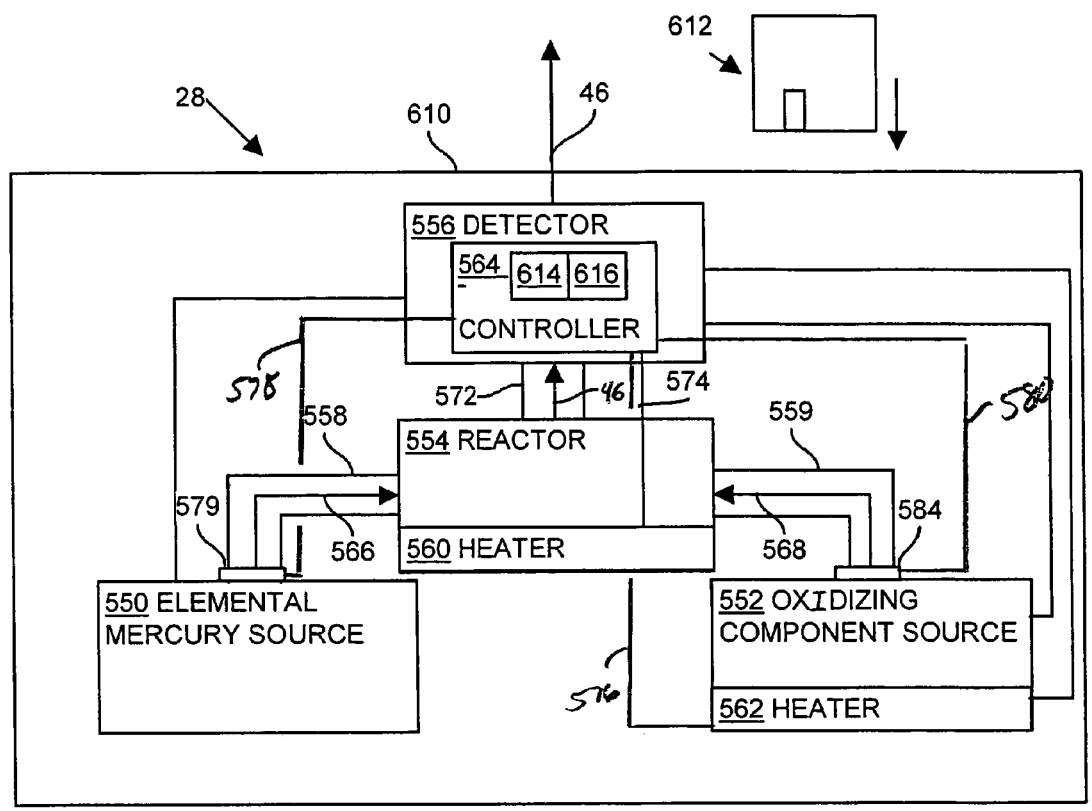
FIG. 12 illustrates an arrangement of a mercury system calibrator as used within the mercury monitoring system of FIG. 1.

FIG. 12 illustrates an arrangement of the calibrator 28. The calibrator 28 includes an elemental mercury source 550, an oxidizing component source 552, and a reactor 554 coupled to the elemental mercury source 550 and the oxidizing component source 552.

The elemental mercury source 550 is connected to the reactor by a conduit 558 and provides a stream of elemental mercury 566, having a known concentration, to the reactor 554. For example, in one arrangement, the elemental mercury source 550 includes a vapor generator with liquid elemental mercury. The liquid elemental mercury evaporates from application of a particular pressure and temperature. The vapor generator further passes a flow of gas or air (e.g., substantially mercury-free gas) through the evaporated elemental mercury and delivers the vaporized mercury to the reactor 554 as a vapor stream 566 having a known (e.g., operator determined) concentration of vaporized mercury within the vapor stream. In another arrangement, the elemental mercury source 550 includes a permeation device. The permeation device contains elemental mercury in a two-phase state (liquid and gas). At a substantially constant temperature, the permeation device emits gaseous elemental mercury at a substantially constant rate through a permeable element (e.g., Teflon housing) and the elemental mercury gas 566 is delivered to the reactor 554 via the conduit 558.

The oxidizing component source 552 is connected to the reactor 554 by a conduit 559 and provides a mercury oxidizing component 568 to the reactor 554. For example, the oxidizing component source 552 provides chlorine (e.g., $Cl_2$) to the reactor 554 to oxidize the elemental mercury 566 received by the reactor 554. In one arrangement, the oxidizing component source 552 is configured as a container holding a chlorine generating chemical that upon heating generates chlorine in a gaseous phase.

In one arrangement, the oxidizing component source 552 includes a heater 562 and a mercury oxidizing component 568 such as palladium chloride (e.g., $PdCl_2$) or tungsten chloride in solid form. In such cases, the heater 562 increases the temperature of the palladium chloride within the oxidizing component source 552 to cause thermal separation of the palladium component from the chlorine component. The separated chlorine is then directed from the oxidizing component source 552 to the reactor 554 as chlorine gas 568.

The reactor 554 is configured to receive elemental mercury 566 from the elemental mercury source 550 and the mercury oxidizing component (e.g., chlorine) 568 from the oxidizing component source 552 and combine the oxidizing component 568 with the elemental mercury 566 to form an output or output stream 46 that includes elemental mercury gas (assuming that not all of the mercury from elemental mercury source 550 is oxidized) and mercury chloride ($HgCl_2$) gas. The reactor 554, in one arrangement, defines a chamber for mixing of the elemental mercury gas 566 and the chlorine gas 568 and includes a heater 560, such as a heating coil in thermal communication with the chamber. The heater 560 delivers thermal energy (e.g., heat) to the chamber to promote combining of the elemental mercury gas 566 and the chlorine gas 68 to form mercury chloride ($HgCl_2$).

As indicated above, the calibrator 28 generates measurable concentrations of oxidized mercury for calibrating continuous emission monitoring systems requiring accurate responses to both elemental mercury and oxidized mercury. The following describes an example of operation of the calibrator 28.

Figure 13:
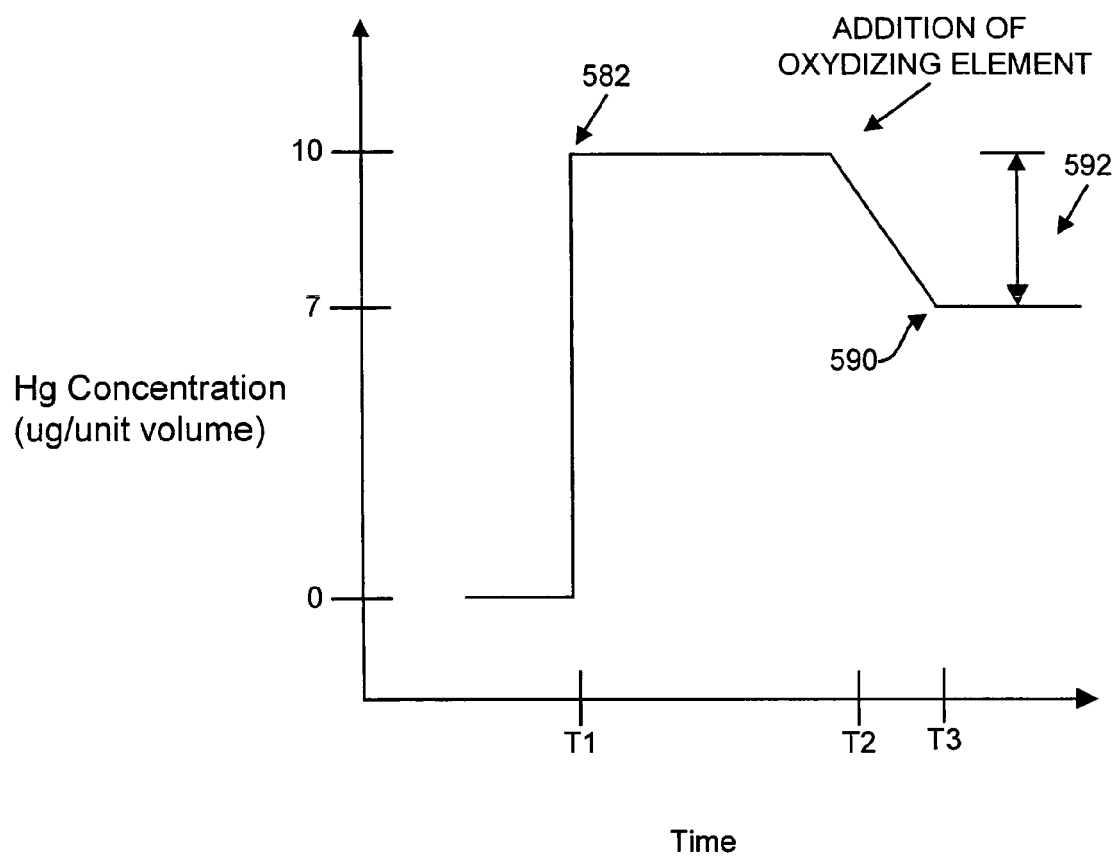
FIG. 13 is a graph illustrating detection of oxidized mercury generated by the mercury system calibrator.

FIG. 13, taken in conjunction with FIG. 12, illustrates a concentration of elemental mercury within the output 46 during operation of the calibrator 28 (e.g., before and after addition of the mercury oxidizing component 568 to the elemental mercury gas 566 held by the reactor 554).

In the calibrator 28, the elemental mercury source 550 delivers a first concentration of elemental mercury 566 to a reactor 554. For example, the elemental mercury source 550 of the calibrator 28 generates an elemental mercury stream 566 having a known or first elemental mercury concentration value, $[Hg^0]_1$. As illustrated in FIG. 13, at a first time T1, the elemental mercury stream 566 (which is flowing from the elemental mercury source 550 via the conduit 558 to the reactor 554) may have a first, known concentration value 582 of 10 micrograms/unit volume.

The oxidizing component source 552 in the calibrator 28 delivers an oxidizing component 568 to the reactor 554, which may be operated at approximately room temperature (e.g., 22° C.). The reactor 554 combines the oxidizing component 568 with the elemental mercury 566. For example, as illustrated in FIG. 13, at a second time T2, the oxidizing component source 552 provides chlorine gas (e.g., $Cl_2$) 568 to the reactor 554 as a fluid flow, carried by the conduit 559, to oxidize the elemental mercury 566 received by the reactor 554. As indicated above, the reactor 554 defines a chamber that allows for mixing of the elemental mercury (e.g., gas) 566 and the chlorine gas 568 to form mercury chloride ($HgCl_2$) gas. In one arrangement, the reactor receives a thermal input (e.g., heat) from the heater 560 to promote rapid combining of the chlorine gas 568 with the elemental mercury 656 to form mercury chloride ($HgCl_2$) gas.

Since the chlorine gas 68 combines with a portion (e.g., a percentage) of the elemental mercury 66 present within the reactor to form mercury oxide gas, as illustrated in FIG. 4 in the interval between the second time T2 and a third time T3, the concentration of elemental mercury within the reactor 54 decreases from the concentration delivered to the reactor 54 from the elemental mercury source 550. For example, the concentration of elemental mercury decreases from a first concentration 82 of 10 micrograms/unit volume to a second concentration 90 of 7 micrograms/unit volume.

The calibrator 28 generates an output 46 having a second concentration of elemental mercury (e.g., at least a portion of the elemental mercury) based upon the combination of the oxidizing component 568 with the elemental mercury 566 and the output having a known concentration of oxidized mercury based upon a difference between the first concentration of elemental mercury and the second concentration of elemental mercury. Since the chlorine gas 568 combines with a portion (e.g., a percentage) of the elemental mercury 566 present within the reactor to form mercury oxide gas, as illustrated in FIG. 13 in the interval between the second time T2 and a third time T3, the concentration of elemental mercury within the reactor 554 decreases from the concentration delivered to the reactor 554 from the elemental mercury source 550. For example, the concentration of elemental mercury decreases from a first concentration 582 of 10 micrograms/unit volume to a second concentration 590 of 7 micrograms/unit volume. The difference between the first concentration of elemental mercury and the second concentration of elemental mercury allows a user to determine the concentration of oxidized mercury within the output 46. The calibrator 28 releases the output 46 (e.g., output stream) having the second concentration 590 to the converter 24.

Returning to FIG. 12, in one arrangement, the calibrator 28 includes a detector 556. The detector 556 is connected to the reactor 554 via a conduit 572 and is configured to receive the output stream 46 from the reactor 554. The detector 556 includes a controller 564, such as a processor 614 and a memory 616. The detector 556, such as an atomic fluorescence spectrometer, in conjunction with the controller 564, is configured to detect a concentration of elemental mercury within the output 46. For example, the detector 556 utilizes atomic fluorescence spectroscopy to measure the concentration of elemental mercury present within the reactor output 46. The detector 556 (e.g., the controller 564 of the detector 556) also compares the second concentration 590 of elemental mercury (see again FIG. 13) present within the reactor output 46 with the known concentration of elemental mercury 566 produced by the elemental mercury source 550. The detected difference in elemental concentrations allows for the calculation of a concentration of oxidized mercury within the output 46, as described below.

For example, the detector 556 calculates a difference between the first concentration 582 of elemental mercury and the second concentration 590 of elemental mercury within the output 46 to detect a concentration of oxidized mercury within the output 46. That is, the controller 564 receives a second concentration value of the elemental mercury within the output 46 from the detector 556 and subtracts that second, reduced elemental mercury concentration $[Hg^0]_2$ from the first, known elemental mercury concentration $[Hg^0]_1$. The difference between $[Hg^0]_1$ and $[Hg^0]_2$, illustrated in FIG. 13 as a change 592 in the elemental mercury concentration, is substantially equal to the concentration of oxidized mercury (e.g., $HgCl_2$) produced by the calibrator 28. By providing oxidized mercury at a measurable concentration, the calibrator 28 allows a user to calibrate the continuous emission monitoring system 20 for accurate response to both elemental mercury and oxidized mercury.

Returning to FIG. 12, in one arrangement, the controller 564 controls the thermal output of the heater 560 of the reactor 554 through an electrical line 574. The controller 564 activates the heater 560 associated with the reactor 554 to provide heat to the elemental mercury 566 and oxidizing component 568 within the reactor 554, promoting the formation of oxidized mercury. The controller 564 may also adjust the thermal output of (e.g., level of heat provided by) the heater 560 to adjust the extent of combination of the elemental mercury 566 and oxidizing component 568 and thus the concentration of oxidized mercury present within the output 46.

During operation, the controller 564 calculates the concentration of oxidized mercury within the output 46 of the reactor 554 (which is also the output 46 of the detector 556). In the case, for example, where a particular application requires the calibrator 28 to produce oxidized mercury at a particular preset concentration, the controller 564 compares a preset oxidized mercury concentration value (e.g., threshold value) with a calculated oxidized mercury value. If the preset oxidized mercury concentration value is not equal to the calculated oxidized mercury value, the controller 564 adjusts the thermal output of the heater 560 to either raise or lower the temperature of the reactor 554 (e.g., raise or lower the temperature of the elemental mercury 566 and the oxidizing component 568 within the reactor 554) so as to vary the extent of the reaction between elemental mercury 566 and the oxidizing component 568, thereby adjusting the concentration of mercury oxide present within the output 46.

In one arrangement, the controller 564 is electrically connected to, and controls, the heater 562 associated with the oxidizing component source 552 through an electrical line 576. As indicated above, in one arrangement, the oxidizing component 568 contained by the oxidizing component source 552 is an oxidized metal, such as palladium chloride (e.g., $PdCl_2$) or tungsten chloride. During operation, the controller 564 activates the heater 562 to provide heat (e.g., the heater operates at a temperature of approximately 300° C.) to the oxidized metal, liberating chlorine gas, which flows from the oxidizing component source 552 to the reactor 554.

The controller 564, in one arrangement, is also configured to adjust a thermal output of (e.g., a level of heat provided by) the heater 562 to adjust the extent of decomposition of the oxidized metal into a metal component and an oxidizing component 568. By adjusting the extent of decomposition, the controller 564 can adjust the amount of the oxidizing component 568 delivered by the oxidizing component source 552 to the reactor 554 and thereby adjust the concentration of oxidized mercury present within the output 46.

During operation, the controller 564 calculates the concentration of oxidized mercury within the output 46. In the case, for example, where a particular application requires the calibrator 28 to produce oxidized mercury at a particular preset concentration, the controller 564 compares a preset oxidized mercury concentration value (e.g., threshold value) with a calculated oxidized mercury value. If the preset oxidized mercury concentration value is not equal to the calculated oxidized mercury value, the controller 564 adjusts the thermal output of the heater 562 to either increase or decrease the rate of separation of the oxidized metal into a metal component and an oxidizing component 568. By changing the extent of decomposition of the oxidized metal, the controller 564 increases or decreases the amount of the oxidizing component 568 (e.g., chlorine gas) available within the reactor 554 to chemically combine with the elemental mercury 566 within the reactor 554. As a result, the controller 564 adjusts the concentration of mercury oxide created within the reactor 554 and provided within the output 46 from the reactor 554.

In one arrangement, the controller 564 adjusts the amount of the elemental mercury 566 provided to the reactor 554 by the elemental mercury source 550 during operation. For example, in one arrangement, the controller 564 is electrically connected through an electrical line 578 to a valve 579 associated with the elemental mercury source 550 and in flow communication with the conduit 558. By increasing or decreasing the flow volume of elemental mercury 566 to the reactor 554, the controller 564 adjusts the amount of elemental mercury 566 within the reactor 554 available to chemically combine with the oxidizing component present. As a result, by adjusting the amount of the elemental mercury 566 provided to the reactor 554, the controller 564 adjusts the concentration of mercury oxide created within the reactor 554 and provided within the output 46 from the reactor 554.

For example, during operation, the controller 564 calculates the concentration of oxidized mercury within the output 46. The controller 564 compares a preset oxidized mercury concentration value (e.g., a threshold value) with the calculated oxidized mercury value. If the preset oxidized mercury concentration value is not equal to the calculated oxidized mercury value, the controller 564 adjusts (e.g., increases or decreases) the amount of the elemental mercury 566 delivered to the reactor 554, such as by adjusting the valve 579 of the elemental mercury source 550. By adjusting the amount of the elemental mercury 566 provided to the reactor 554, the controller 564 adjusts the concentration of mercury oxide created within the reactor 554 and provided within the output 46 from the reactor 554.

In one arrangement, the controller 564 adjusts the amount of the oxidizing component 568 provided to the reactor 554 by the oxidizing component source 552 during operation. For example, in one arrangement, the controller 564 is electrically connected through an electrical line 580 to a valve 584 associated with the oxidizing component source 552 and in flow communication with the conduit 559. By increasing or decreasing the flow amount of the oxidizing component 568 to the reactor 554, the controller 564 adjusts the amount of the oxidizing component 568 within the reactor 554 available to chemically combine with the elemental mercury 566 present. As a result, by adjusting the amount of the oxidizing component 568 provided to the reactor 554, the controller 564 adjusts the concentration of mercury oxide created within the reactor 554 and provided within the output 46 from the reactor 554.

For example, during operation, the controller 564 calculates the concentration of oxidized mercury within the output 46. The controller 564 compares a preset oxidized mercury concentration value (e.g., a threshold value) with the calculated oxidized mercury value. If the preset oxidized mercury concentration value is not equal to the calculated oxidized mercury value, the controller 564 adjusts (e.g., increases or decreases) the volume of the oxidizing component 568 delivered to the reactor 554, such as by adjusting the valve 584 of the elemental mercury source 550. By adjusting the volume of the oxidizing component 568 provided to the reactor 554, the controller 564 adjusts the concentration of mercury oxide created within the reactor 554 and provided within the output 46 from the reactor 554.

Figure 14:
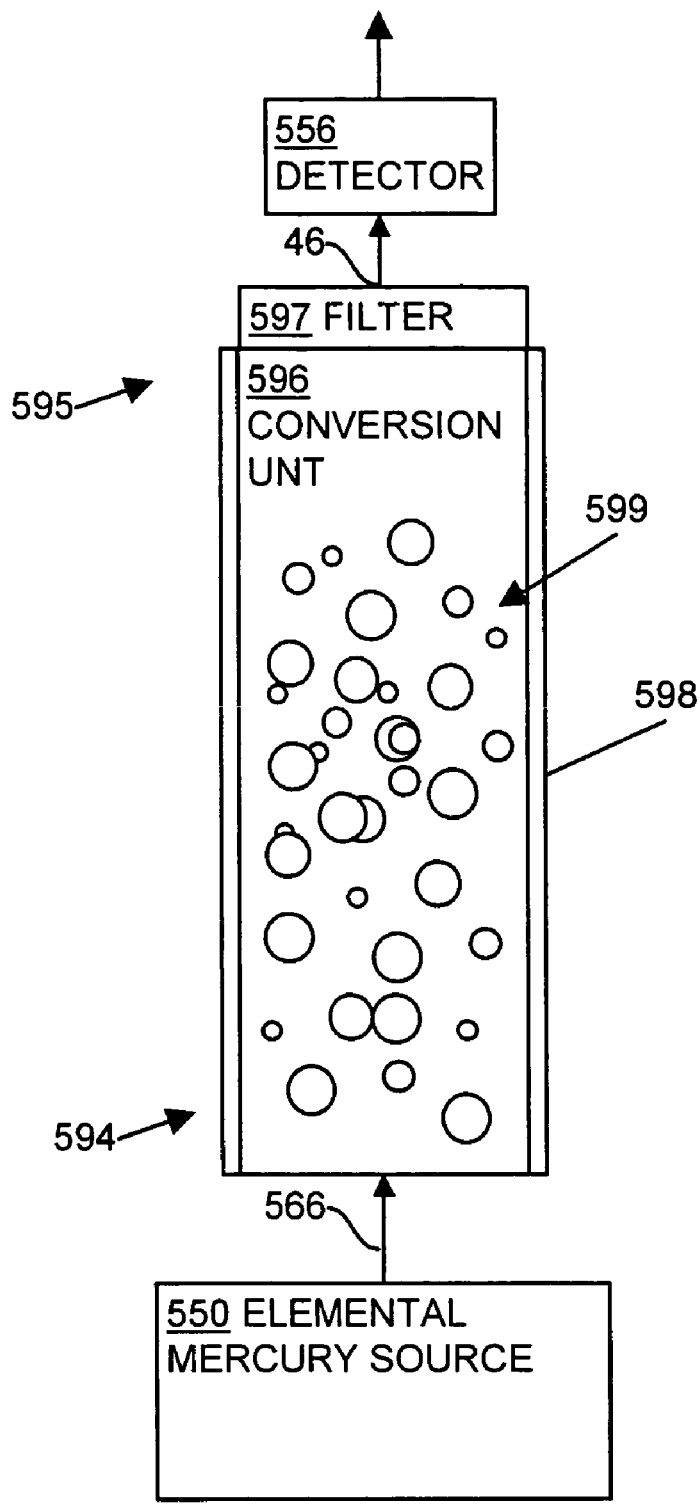
FIG. 14 illustrates an arrangement of a mercury system calibrator as used within the mercury monitoring system of FIG. 1.

FIG. 14 illustrates an arrangement of the calibrator 28 where the reactor and the oxidizing component source (elements 554 and 552 of the calibrator 28 of FIG. 12) form a single, integrated conversion unit 596. Such an arrangement minimizes the number of components required by the calibrator 28 to generate a known concentration of mercury oxide.

The conversion unit 596 has a first end 594 and a second end 595. The first end 594 is connected to the elemental mercury source 550 and is operable to direct elemental mercury 566 through the conversion unit 596 toward the second end 595. The second end 595 is connected to the detector 556 and is operable to direct an output 46 (e.g., a combination of elemental mercury and oxidized mercury in gaseous phase) toward the detector 556. The conversion unit 596 includes, or its second end 595 is connected to, a filter 597 and a heater 598 and contains an oxidized metal 599, such as palladium chloride (e.g., $PdCl_2$).

The heater 598 is operable to heat materials within the conversion unit 596 and serves a dual purpose. First, the heater 598 is configured to increase the temperature of oxidized metal 599 within the conversion unit 596 to cause thermal separation of the metal component from the oxidizing component. Second, the heater 598 is configured to deliver thermal energy or heat to the conversion unit 596 to increase the temperature of the elemental mercury gas 566 and the oxidizing component (e.g., chlorine gas) 568 present within the conversion unit 596. Such an increase in temperature promotes combination of the elemental mercury gas 566 and the chlorine gas 568 to form mercury chloride ($HgCl_2$).

Returning to FIG. 12, the calibrator 28, in one arrangement, is configured as a computerized device 610. A computer program product 612 includes an application or logic instructions that are loaded into the computerized device 610 to configure the device 610 to perform as a calibrator 28.

The computerized device 610 includes the controller 564 that, in one arrangement, includes a memory 614 and a processor 616. The memory 614 can be of any type of volatile or non-volatile memory or storage system such as a computer memory (e.g., random access memory (RAM), read only memory (ROM), or another type of memory) disk memory, such as hard disk, floppy disk, optical disk, for example. The memory 614 is encoded with logic instructions and/or data that, in one embodiment of the computerized device 610, form a calibrator application configured according to embodiments of the calibrator 28. In other words, the calibrator application represents software coding instructions and/or data that reside within the memory or storage 614, or within any computer readable medium accessible to the computer device 610.

The processor 616 may be any type of circuitry or processing device such as a central processing unit, controller, application specific integrated circuit, programmable gate array, or other circuitry that can access the calibrator application encoded within the memory 614 in order to run, execute, interpret, operate, or otherwise perform the calibrator application logic instructions. In other words, in another embodiment of the computer device 610, a calibrator process represents one or more portions of the logic instructions of the calibrator application while being executed or otherwise performed on, by, or in the processor 616 within the computerized device 610.

While this invention has been particularly shown and described with reference to preferred embodiments thereof, it will be understood by those skilled in the art that various changes in form and details may be made therein without departing from the spirit and scope of the invention as defined by the appended claims.

For example, as illustrated in FIG. 1, the probe 22 retrieves a gas sample 32 from a stack 34 and delivers the gas sample 32 to the converter 24 by way of a heated conduit 38. The heated conduit 38 limits condensation of the gas sample 32 and "sticking" of vaporized mercury (e.g., $Hg^{+2}$ species) to the conduit 38. Such illustration is by way of example only. In one arrangement the converter 24 is oriented in close proximity to the gas sample source (e.g., stack). For example, the converter 24 can be located near the point of extraction of sample 32 from the utility stack 34 (e.g. in relatively close proximity to the probe 22) or built into the extraction probe 22 (e.g., integrally formed as part of the probe 22). Such a configuration minimizes or eliminates the necessity for the heated conduit 38 between the probe 22 and the converter 24.

Also, in one arrangement as described with respect to FIG. 2, the heater is 62 is configured as having first heater portion 62-1 oriented in thermal communication with the first chamber 56 and a second heater portion 62-2 oriented in thermal communication with the second chamber 58 of the converter 24. As described, the first heater portion 62-1 may heat the gas sample 32 to a temperature of approximately 750° C. in order to thermally crack the elemental mercury components 80 from the oxidizing components 84. Also as described, the second heater portion 62-2 also heats the gas sample 32 within the second chamber 58 to temperature of approximately 750° C. to maintain separation of the elemental mercury components 80 from the oxidizing components 84. Such description is by way of example only. In one arrangement, the second heater 62-2 operates independently of the first heater 62-1 and maintains the second chamber 58 at a different temperature than that of the first chamber 56—e.g., greater than, less than, or equal to the temperature of the gas sample in the first chamber 56.

As indicated above, with respect to FIGS. 8 and 11, the analyzer 26 includes a fluorescence quenching reduction mechanism 254 configured as either a pressure reduction apparatus and/or as an oxygen depleted gas source 328. In one arrangement, the fluorescence quenching reduction mechanism 254 is formed as the combination of the pressure reduction apparatus (e.g., the pump 64 operating in conjunction with the flow restrictor or nozzle 239) and the oxygen depleted gas source 328 (see FIG. 10) so as to further reduce the effect of quenching on the fluorescence of elemental mercury 255 within the gas sample 32.

Also as indicated above, with reference to FIG. 8, the pressure reduction apparatus 254 includes a vacuum pump 64 operating in conjunction with a flow restrictor 239 (e.g., a nozzle) where the inlet 256 of the housing 250 includes the flow restrictor 239. In one arrangement, the flow restrictor 239 is located upstream from the inlet 256 of the analyzer 26.

With respect to FIG. 12, in one example, the detector 556 forms part of the calibrator 28. Such illustration and description is by way of example only. In an alternate arrangement, the calibrator 28 utilizes an external detector (e.g., a detector external to) the calibrator. For example, the calibrator 28 may utilize the analyzer 26 of the system 20 to perform the functions of the detector 556 described above.

FIG. 12 illustrates the detector 556 as having a single controller 564 configured to operate components of the calibrator (e.g., the elemental mercury source 550, the reactor heater 560, the oxidizing component source 552, and the oxidizing component source heater 562). Such illustration is by way of example only; in another arrangement the calibrator 28 includes separate controllers each performing one or more functions of the single controller 564 described above.

As indicated above, also with respect to FIG. 12, during operation elemental mercury 566 flows from the elemental mercury source 550 to the reactor 554 via the conduit 558. Also during operation, the oxidizing component 568, such as chlorine gas, flows from the oxidizing component source 552 to the reactor 554 via the conduit 559. In another arrangement, the conduit 58 flows elemental mercury 66 past the oxidizing component source 52 to the reactor 54. The oxidizing component source 52 delivers the oxidizing component 68 to the reactor 54 by way of passive diffusion. Passive diffusion of the oxidizing component 68 limits or eliminates the need for a pump to force or draw the oxidizing component 68 from the oxidizing component source 52 and into the reactor 54.

FIG. 12 illustrates an arrangement of the calibrator 28 as including the elemental mercury source 550, the oxidizing component source 552, and the reactor as a single "unit". In one arrangement, the elemental mercury source 550 and the oxidizing component source 552 are located at two separate locations. For example, the elemental mercury source 550 can be located within an instrument rack while the oxidizing component source 552 is located in or within proximity to the probe 22.

What is claimed is:

1. A mercury monitoring system comprising:
a probe configured to retrieve a fluid sample from a fluid source;
an oxidized mercury converter in fluid communication with the probe, the oxidized mercury converter comprising:
a housing having an inlet for admitting a fluid sample into a chamber defined by the housing and an outlet,
a heater operable to heat the fluid sample admitted into the chamber defined by the housing so as to convert oxidized mercury present within the fluid sample into an elemental mercury component and an oxidizing component, and a pressure reduction apparatus operable to decrease the pressure of the fluid sample; and a mercury analyzer in fluid communication with the outlet of the oxidized mercury converter, the mercury analyzer configured to receive the fluid sample from the oxidized mercury converter and operable to detect a concentration of elemental mercury within the fluid sample.

2. The mercury monitoring system of claim 1 wherein the pressure reduction apparatus is operable to reduce the pressure of the fluid sample to between approximately 0.1 and 0.3 atmospheres.

3. The mercury monitoring system of claim 1 comprising a chemical scrubber oriented in fluid communication with the oxidized mercury converter so that the fluid sample passing through the converter flows through, or in proximity to, the chemical scrubber.

4. The mercury monitoring system of claim 1 wherein the housing has a second inlet for receipt of substantially mercury-free dilution fluid.

5. The mercury monitoring system of claim 1 wherein the heater is configured to heat a fluid sample to a temperature of between approximately 650 degrees Celsius and 800 degrees Celsius.

6. The mercury monitoring system of claim 1 wherein the pressure reduction apparatus comprises a flow restrictor oriented in fluid communication with the chamber defined by the housing.

7. The mercury monitoring system of claim 1 comprising a flow bypass element in fluid communication with the probe, the flow bypass element configured to direct the fluid sample to the mercury analyzer, bypassing the oxidized mercury converter.

8. The mercury monitoring system of claim 1 comprising a calibrator in fluid communication with the oxidized mercury converter, the calibrator having:
   a reactor;
   an elemental mercury source in fluid communication with the reactor, the elemental mercury source configured to deliver a first concentration of elemental mercury to the reactor; and
   an oxidizing component source in fluid communication with the reactor, the oxidizing component source configured to deliver an oxidizing component to the reactor, the reactor operable to combine the oxidizing component with at least a portion of the elemental mercury to form an output having (i) a second concentration of elemental mercury and (ii) a concentration of oxidized mercury determinable as the difference between the first concentration of elemental mercury and the second concentration of elemental mercury.

9. A mercury monitoring system comprising:
   a probe configured to retrieve a fluid sample from a fluid source;
   an oxidized mercury converter in fluid communication with the probe, the oxidized mercury converter operable to convert oxidized mercury present within the fluid sample into an elemental mercury component and an oxidizing component; and
   a mercury analyzer in fluid communication with the oxidized mercury converter, the mercury analyzer having:
      a housing having an inlet for receiving a fluid sample from the converter, an outlet for discharging the fluid sample, and defining a chamber for containing the fluid sample,
      a fluorescence assembly in optical communication with the chamber, the fluorescence assembly configured to induce fluorescence of elemental mercury present within the fluid sample and detect a fluorescence signal of the fluid sample based upon fluorescence of at least a portion of the elemental mercury, and
      a fluorescence quenching reduction mechanism in fluid communication with the chamber, the fluorescence quenching reduction mechanism configured to limit fluorescence quenching of the fluid sample.

10. The mercury monitoring system of claim 9 wherein the fluorescence quenching reduction mechanism comprises a pressure reduction apparatus for providing a reduced pressure of a fluid sample within the chamber, relative to the pressure of the fluid source.

11. The mercury monitoring system of claim 10 wherein the pressure reduction comprises a pump operable to draw a fluid sample into the chamber via the inlet and a flow restrictor for restricting flow of the fluid sample prior to its entry into the chamber.

12. The mercury monitoring system of claim 9 wherein the fluorescence quenching reduction mechanism comprises a source of oxygen depleted gas in fluid communication with the chamber.

13. The mercury monitoring system of claim 9 wherein the fluorescence assembly comprises a light source assembly configured to induce fluorescence of elemental mercury present within the fluid sample and a detector assembly configured to detect the fluorescence signal of the fluid sample based upon fluorescence of at least a portion of the elemental mercury.

14. The mercury monitoring system of claim 13 wherein the light source assembly comprises an input polarizing element oriented in optical communication with the light source assembly.

15. The mercury monitoring system of claim 14 wherein the detector assembly comprises an output polarizing element oriented in optical communication with the detector assembly.

16. The mercury monitoring system of claim 9 comprising a flow bypass element in fluid communication with the probe, the flow bypass element configured to direct the fluid sample to the mercury analyzer, bypassing the oxidized mercury converter.

17. A mercury monitoring system comprising:
   a probe configured to retrieve a fluid sample from a fluid source;
   an oxidized mercury converter in fluid communication with the probe, the oxidized mercury converter comprising:
      a converter housing having an inlet for admitting a fluid sample into a converter chamber defined by the converter housing and an outlet,
      a heater operable to heat the fluid sample admitted into the converter chamber defined by the converter housing so as to convert oxidized mercury present within the fluid sample into an elemental mercury component and an oxidizing component, and
      a pressure reduction apparatus operable to decrease the pressure of the fluid sample; and
   a mercury analyzer in fluid communication with the outlet of the oxidized mercury converter, the mercury analyzer and the mercury analyzer having:
      an analyzer housing having an inlet configured to receive a reduced pressure fluid sample from the oxidized mercury converter, an outlet for discharging the reduced pressure fluid sample, and defining an analyzer chamber for containing the fluid sample, and
      a fluorescence assembly in optical communication with the analyzer chamber, the fluorescence assembly configured to induce fluorescence of elemental mercury present within the fluid sample and detect a fluorescence signal of the fluid sample based upon fluorescence of at least a portion of the elemental mercury.

18. The mercury monitoring system of claim 17 wherein the pressure reduction apparatus is operable to reduce the pressure of the fluid sample to between approximately 0.1 and 0.3 atmospheres.

19. The mercury monitoring system of claim 17 comprising a chemical scrubber oriented in fluid communication with the oxidized mercury converter so that the fluid sample passing through the converter flows through, or in proximity to, the chemical scrubber.

20. The mercury monitoring system of claim 17 wherein the analyzer housing has a second inlet for receipt of substantially mercury-free dilution fluid.

21. The mercury monitoring system of claim 17 comprising a calibrator in fluid communication with the oxidized mercury converter, the calibrator having:
  a reactor;
  an elemental mercury source in fluid communication with the reactor, the elemental mercury source configured to deliver a first concentration of elemental mercury to the reactor; and
  an oxidizing component source in fluid communication with the reactor, the oxidizing component source configured to deliver an oxidizing component to the reactor, the reactor operable to combine the oxidizing component with at least a portion of the elemental mercury to form an output having (i) a second concentration of elemental mercury within the output and (ii) a concentration of oxidized mercury determinable as the difference between the first concentration of elemental mercury and the second concentration of elemental mercury.

22. The mercury monitoring system of claim 17 wherein the mercury analyzer comprises a fluorescence quenching reduction mechanism in fluid communication with the analyzer chamber, the fluorescence quenching reduction mechanism configured to limit fluorescence quenching of the fluid sample.

23. The mercury monitoring system of claim 22 wherein the fluorescence quenching reduction mechanism comprises a source of oxygen depleted gas in fluid communication with the analyzer chamber.

24. The mercury monitoring system of claim 17 wherein the fluorescence assembly comprises a light source assembly configured to induce fluorescence of elemental mercury present within the fluid sample and a detector assembly configured to detect the fluorescence signal of the fluid sample based upon fluorescence of at least a portion of the elemental mercury.

25. The mercury monitoring system of claim 1 comprising a calibrator including:
  a reactor containing an oxidizing component source and having an inlet and an outlet, with the outlet in fluid communication with the oxidized mercury converter so as to direct an output thereto;
  an elemental mercury source operable to deliver a first concentration of elemental mercury to the inlet of the reactor;
  the reactor operable to produce an oxidizing component and to combine the oxidizing component with at least a portion of the elemental mercury to form an output having (i) a second concentration of elemental mercury and (ii) a concentration of oxidized mercury determinable as the difference between the first concentration of elemental mercury and the second concentration of elemental mercury.

26. A method for monitoring the presence of mercury within a gas sample comprising:
  heating a fluid sample having oxidized mercury to convert the oxidized mercury present within the fluid sample into an elemental mercury component and an oxidizing component;
  reducing a pressure of the heated gas sample to limit recombination of the elemental mercury component and the oxidizing component;
  inducing fluorescence of elemental mercury present within the reduced pressure fluid sample; and
  detecting a fluorescence signal of the fluid sample based upon fluorescence of the elemental mercury within the fluid sample, the fluorescence signal proportional to a concentration of elemental mercury within the fluid sample.

27. A mercury monitoring system comprising:
  a probe configured to retrieve a fluid sample from a fluid source;
  an oxidized mercury converter in fluid communication with the probe, the oxidized mercury converter comprising:
    a housing having an inlet for admitting a fluid sample into a chamber defined by the housing and an outlet,
    a heater operable to heat the fluid sample admitted into the chamber defined by the housing so as to convert oxidized mercury present within the fluid sample into an elemental mercury component and an oxidizing component;
  a mercury analyzer in fluid communication with the outlet of the oxidized mercury converter, the mercury analyzer configured to receive the fluid sample from the oxidized mercury converter and operable to detect a concentration of elemental mercury within the fluid sample; and
  a pressure reduction apparatus operable to decrease the pressure of the fluid sample relative to at least one of the oxidized mercury converter and the mercury analyzer.

28. The mercury monitoring system of claim 10 wherein the pressure reduction apparatus is operable to reduce the pressure of a fluid sample, relative to the pressure of the fluid source, to reduce an effect of Raleigh scattering within the fluid sample.

* * * * *